US009790189B2

(12) United States Patent
Lücking et al.

(10) Patent No.: US 9,790,189 B2
(45) Date of Patent: Oct. 17, 2017

(54) DISUBSTITUTED 5-FLUORO PYRIMIDINE DERIVATIVES CONTAINING A SULFONDIIMINE GROUP

(71) Applicant: Bayer Pharma Aktiengesellschaft, Berlin (DE)

(72) Inventors: Ulrich Lücking, Berlin (DE); Arne Scholz, Berlin (DE); Philip Lienau, Berlin (DE); Gerhard Siemeister, Berlin (DE); Rolf Bohlmann, Berlin (DE); Ulf Bömer, Glienicke (DE)

(73) Assignee: Bayer Pharma Aktiengesellschaft, Berlin (DE)

(*) Notice: Subject to any disclaimer, the term of this patent is extended or adjusted under 35 U.S.C. 154(b) by 0 days.

(21) Appl. No.: 15/300,755

(22) PCT Filed: Mar. 27, 2015

(86) PCT No.: PCT/EP2015/056757
§ 371 (c)(1),
(2) Date: Sep. 29, 2016

(87) PCT Pub. No.: WO2015/150273
PCT Pub. Date: Oct. 8, 2015

(65) Prior Publication Data
US 2017/0015634 A1    Jan. 19, 2017

(30) Foreign Application Priority Data

Apr. 1, 2014 (EP) .................... 14163067

(51) Int. Cl.
C07D 239/42  (2006.01)
A61K 31/505  (2006.01)
A61K 31/506  (2006.01)
C07D 407/04  (2006.01)
C07D 405/04  (2006.01)
C07D 401/12  (2006.01)
C07C 309/30  (2006.01)

(52) U.S. Cl.
CPC .......... *C07D 239/42* (2013.01); *A61K 31/505* (2013.01); *A61K 31/506* (2013.01); *C07C 309/30* (2013.01); *C07D 401/12* (2013.01); *C07D 405/04* (2013.01); *C07D 407/04* (2013.01)

(58) Field of Classification Search
CPC .. C07D 239/42; C07D 401/12; C07D 405/04; C07D 407/04; A61K 31/505; A61K 31/506
USPC ................. 544/330, 332; 514/275
See application file for complete search history.

(56) References Cited

U.S. PATENT DOCUMENTS

2004/0209895 A1  10/2004  Luecking et al.
2005/0176743 A1   8/2005  Luecking et al.
2010/0184789 A1   7/2010  Wabnitz et al.
2011/0028492 A1   2/2011  Barsanti et al.
2011/0306602 A1  12/2011  Wabnitz et al.

FOREIGN PATENT DOCUMENTS

| EP | 2527332 | 11/2012 |
| WO | WO-02059110 | 8/2002 |
| WO | WO-2005037800 | 4/2005 |
| WO | WO-2006064251 | 6/2006 |
| WO | WO-2008028590 | 3/2008 |
| WO | WO-2008060248 | 5/2008 |
| WO | WO-2008079918 | 7/2008 |
| WO | WO-2008079933 | 7/2008 |
| WO | WO-2008/129070 A1 | 10/2008 |
| WO | WO-2008129071 | 10/2008 |
| WO | WO-2008129080 | 10/2008 |
| WO | WO-2008132138 | 11/2008 |
| WO | WO-2009029998 | 3/2009 |
| WO | WO-2009118567 | 10/2009 |
| WO | WO-2011116951 | 9/2011 |
| WO | WO-2012117059 | 9/2012 |
| WO | WO-2013/037894 A1 | 3/2013 |
| WO | WO-2013/037896 A1 | 3/2013 |
| WO | WO-2014060376 | 4/2014 |
| WO | WO-2014076028 | 5/2014 |
| WO | WO-2014076091 | 5/2014 |
| WO | WO-2015001021 | 1/2015 |
| WO | WO-2015136028 | 9/2015 |

OTHER PUBLICATIONS

Simone, Oncology: Introduction, Cecil Textbook of Medicine, 20th Edition, vol. 1, pp. 1004-1101 O, 1996.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Razonable et al., PubMed Abstract (Herpes 10(3):60-5), 2003.*
Blain et al., Differential Interaction of the Cyclin-dependent Kinase (Cdk) Inhibitor p27Kip1 with Cyclin A-Cdk2 nad Cyclin D2-Cdk4, The Journal of Biological Chemistry, vol. 272, No. 41, pp. 25863-25872, 1997.*
LuValle et al., Cell Cycle Control in Growth Plate, Frontiers in Biosciences, 5, d493-503, May 2000.*

(Continued)

*Primary Examiner* — Deepak Rao
(74) *Attorney, Agent, or Firm* — Morrison & Foerster LLP

(57) ABSTRACT

The present invention relates to 5-fluoro pyrimidine derivatives containing a sulfondiimine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

26 Claims, No Drawings

(56) References Cited

OTHER PUBLICATIONS

International Search Report and Written Opinion mailed on May 13, 2015, for PCT Patent Application No. PCT/EP2015/056757, filed on Mar. 27, 2015, 12 pages.
Allenmark, S. et al. (1983). "Enantioselective Liquid Chromatographic Retention of a Series of Sulfoxides and N-substituted Sulfoximines on Chiral Stationary Phases," *Acta Chemica Scandinavica B* 37: 325-328.
Bark-Jones, S.J. et al. (2006). "EBV EBNA 2 stimulates CDK9-dependent transcription and RNA polymerase II phosphorylation on serine 5," *Oncogene* 25: 1775-1785.
Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," *Journal of Medicinal Chemistry* 22(4): 418-424.
Bauer, V.J. et al. (Oct. 1966). "The Reactions of Carbamoyl Azides with Sulfur Nucleophiles," *Journal of Organic Chemistry* 31: 3440-3441.
Berge, S.M. et al. (Jan. 1977). "Pharmaceutical Salts," *Journal of Pharmaceutical Sciences* 66(1): 1-19.
Bolm, C. et al. (1998). "Palladium-Catalyzed Carbon-Nitrogen Bond Formation: A Novel, Catalytic Approach towards N-Arylated Sulfoximines," *Tetrahedron Letters* 39: 5731-5734.
Bolm, C. et al. (2000). "Palladium-Catalyzed N-Arylation of Sulfoximines with Aryl Bromides and Aryl Iodides," *Journal of Organic Chemistry* 65: 169-175.
Bolm, C. et al. (Feb. 2000). "Catalytic Coupling of Aryl Sulfonates with $sp^2$-Hybridized Nitrogen Nucleophiles: Palladium- and Nickel-catalyzed Synthesis of N-Aryl Sulfoximines," *Synthesis* 7: 911-913.
Bolm, C. et al. (2001). "Synthesis of Pseudopeptides with Sulfoximines as Chiral Backbone Modifying Elements," *Chem. Eur. J.* 7(5): 1118-1128.
Bolm, C. et al. (2002). "A Mild Synthetic Procedure for the Preparation of N-Alkylated Sulfoximines," *Synthesis* 7: 879-887.
Cho, G.Y., et al. (2005). "Synthesis and Palladium-Catalyzed Coupling Reaction of Enantiopure p-Bromophenyl Methyl Sulfoximine," *J. Org. Chem.* 70(6): 2346-2349.
Cho, S. et al. (May 1, 2010). "CYCLINg through transcription Posttranslational modification of P-TEFb regulate transcription elongation," *Cell Cycle* 9(9): 1697-1705.
Copeland, R. A. et al. (2006). "Drug-target residence time and its implications for lead optimization," *Nature Reviews Drug Discovery* 5: 730-739.
Craig, D. et al. (1995). "Asymmetric Intramolecular Diels-Alder Reactions of Sulfoximine-activated Trienes," *Tetrahedron* 51(21): 6071-6098.
Cram, D.J. (Dec. 16, 1970). "Stereochemistry of Sulfur Compounds. I. Stereochemical Reactions Cycles Involving an Open Chain Sulfoxide, Sulfimide, and Sulfoximide," *Journal of the American Chemical Society* 92(25): 7369-7384.
De Meijere, A. et al. (2004). "Metal-Catalyzed Cross-Coupling Reactions," *WILEY-VCH Verlag GmbH & Co. KGaA*, Weinheim, pp. 83-91.

Dey, A. et al. (Aug. 1, 2007). "HEXIM1 and the Control of Transcription Elongation from Cancer and Inflammation to AIDS and Cardiac Hypertrophy," *Cell Cycle* 6(15): 1856-1863.
Füger, B. et al. (2009). "Ring-Closing Enyne Metathesis (RCEYM) for the Synthesis of Cyclic Sulfoximines," *Synlett* 10: 1601-1604.
Hackenberger, C.P.R., et al. (2004). "Synthetic and Spectroscopic Investigation of N-Acylated Sulfoximines," *Chem. Eur. J.* 10: 2942-2952.
He, N. et al. (Mar. 14, 2008). "A La-Related Protein Modulates 7SK snRNP Integrity to Suppress P-TEFb-Dependent Transcriptional Elongation and Tumorigenesis," *Molecular Cell* 29: 588-599.
Johnson, C.R. (Nov. 4, 1970). "Preparation and Synthetic Applications of (Dimethylamino)phenyloxosulfonium Methylide," *Journal of the American Chemical Society* 92(22): 6594-6598.
Johnson, C.R. (1978). "Preparation of α-Halo Sulfoximines," *Journal of Organic Chemistry* 43(21): 4136-4140.
Johnson, C.R. et al. (1993). "Alkylation of Sulfoximines and Related Compounds at the Imino Nitrogen under Phase-Transfer Conditions," *Journal of Organic Chemistry* 58(7): 1922-1923.
Jones, M.R. et al. (Apr. 3, 1974). "Stereochemisty of Sulfur Compounds. VII. Course of Substitution at Sulfur Attached to Four Different Ligands," *Journal of the American Chemical Society* 96(7): 2183-2190.
Lücking, U. (2013). "Sulfoximines: A Neglected Opportunity in Medicinal Chemistry," *Angew. Chem. Int.* 52: 9399-9408.
Mancheño, O.G. et al. (2007). "Synthesis of N-(1H)-Tetrazole Sulfoximines," *Organic Letters* 9(15) 2951-2954.
Okamura, H. et al. (2004). "Rhodium-Catalyzed Imination of Sulfoxides and Sulfides: Efficient Preparation of N-Unsubstituted Sulfoximines and Sulfilimines," *Organic Letters* 6(8): 1305-1307.
Polla, M.O. et al. (2004). "Design and synthesis of potent, orally active, inhibitors of carboxypeptidase U (TAFIa)," *Bioorganic & Medicinal Chemistry Letters* 12: 1151-1175.
Sammond, D.M. et al. (2005). "Discovery of a novel and potent series of dianilinopyrimidineurea and urea isostere inhibitors of VEGFR2 tyrosine kinase," *Bioorganic & Medicinal Chemistry Letters* 15: 3519-3523.
Sauer, D.T. et al. (1972). "Bis(perfluoroalkyl)sulfur Oxyimines and Silver Bis(trifluoromethyl)sulfur Oxyimine," *Inorganic Chemistry* 11(2): 238-242.
Stoss, P. et al. (1978). "Transannulare Acylwanderungen in cyclischen Sulfoximiden," *Chem. Ber.* 111: 1453-1463.
Wang, S. et al. (2008). "Cyclin-dependent kinase 9: a key transcriptional regulator and potential drug target in oncology, virology and cardiology," *Trends in Pharmacological Sciences* 29(6): 302-313.
Wang, S. et al. (2010). "Discovery and Characterization of 2-Anilino-4-(Thiazol-5-yl)Pyrimidine Transcriptional CDK Inhibitors as Anticancer Agents," *Chemistry & Biology* 17: 1111-1121.
Yang, Z. et al. (Aug. 19, 2005). "Recruitment of P-TEFb for Stimulation of Transcriptional Elongation by the Bromodomain Protein Brd4," *Molecular Cell* 19: 535-545.
Zhou, M. et al. (Dec. 2004). "Coordination of Transcription Factor Phosphorylation and Histone Methylation by the P-TEFb Kinase during Human Inmmunodeficiency Virus Type 1 Transcription," *Journal of Virology* 78(24): 13522-13533.
Zhou, Q. et al. (Sep. 2006). "The Yin and Yang of P-TEFb Regulation: Implications for Human Immunodeficiency Virus Gene Expression and Global Control of Cell Growth and Differentiation," *Microbiology and Molecular Biology Reviews* 70(3): 646-659.

* cited by examiner

DISUBSTITUTED 5-FLUORO PYRIMIDINE DERIVATIVES CONTAINING A SULFONDIIMINE GROUP

CROSS REFERENCE TO RELATED APPLICATIONS

This application is the national stage of International Application No. PCT/EP2015/056757, filed internationally on Mar. 27, 2015, which claims the benefit of European Patent Application No. 14163067.3, filed on Apr. 1, 2014, the disclosures of which are hereby incorporated by reference in their entireties for all purposes.

The present invention relates to disubstituted 5-fluoro pyrimidine derivatives containing a sulfondiimine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mc1-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO 2009118567 discloses pyrimidine and [1,3,5]triazine derivatives as protein kinase inhibitors, in particular CDK2, CDK7 and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heterorayl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

WO 2011077171 discloses 4,6-disubstituted aminopyrimidine derivatives as inhibitors of CDK9.

WO 2014031937 discloses 4,6-disubstituted aminopyrimidine derivatives as inhibitors of CDK9.

WO 2013037896 discloses disubstituted 5-fluoropyrimidines as selective inhibitors of CDK9.

WO 2013037894 discloses disubstituted 5-fluoropyrimidine derivatives containing a sulfoximine group as selective inhibitors of CDK9.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO 2014060376 discloses substituted 4-(ortho)-fluorophenyl-5-fluoropyrimidin-2-yl amine derivatives containing a sulfone group as selective inhibitors of CDK9.

WO 2014060375 discloses substituted 5-fluoro-N-(pyridin-2-yl)pyridin-2-amine derivatives containing a sulfone group as selective inhibitors of CDK9.

WO 2014060493 discloses substituted N-(pyridin-2-yl)pyrimidin-4-amine derivatives containing a sulfone group as selective inhibitors of CDK9.

WO 2014076028 discloses substituted 4-(ortho)-fluorophenyl-5-fluoropyrimidin-2-yl amine derivatives containing a sulfoximine group as selective inhibitors of CDK9.

WO 2014076091 discloses substituted 5-fluoro-N-(pyridin-2-yl)pyridin-2-amine derivatives containing a sulfoximine group as selective inhibitors of CDK9.

WO 2014076111 discloses substituted N-(pyridin-2-yl)pyrimidin-4-amine derivatives containing a sulfoximine group as selective inhibitors of CDK9.

WO 2015001021 discloses 5-Fluoro-N-(pyridin-2-yl)pyridin-2-amine derivatives containing a sulfoximine group as selective inhibitors of CDK9.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. Nos. 7,618, 968B2, 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

WO2012142329 concerns amino-pyrimidine compounds as inhibitors of TBKL and/or IKK epsilon.

WO2012139499 discloses urea substituted anilino-pyrimidines as inhibitors of various protein kinases.

WO2014106762 discloses 4-pyrimidinylamino-benzenesulfonamide derivatives as inhibitors of polo-like kinase-1.

Sulfondiimines are high-valent sulphur compounds first described by Coliano and Braude in 1964 (J. A. Cogliano, G. L. Braude, J. Org. Chem. 1964, 29, 1397), and since their discovery, they have received only minimal interest in the scientific community (M. Candy, R. A. Hohmann, C. Bolm, Adv. Synth. Catal. 2012, 354, 2928). Thus, there are only very few examples for the use of the sulfondiimine group in medicinal chemistry approaches (see for example a) DE2520230, Ludwig Heumann & Co. GmbH; b) W. L. Mock, J.-T. Tsay, J. Am. Chem. Soc. 1989, 111, 4467).

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
- improved activity and/or efficacy
- beneficial kinase selectivity profile according to the respective therapeutic need
- improved side effect profile, such as fewer undesired side effects, lower intensity of side effects, or reduced (cyto)toxicity
- improved physicochemical properties, such as solubility in water, body fluids, and aqueous formulations, e.g. for intravenous administration
- improved pharmacokinetic properties, allowing e.g. for dose reduction or an easier dosing scheme
- easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines, such as HeLa, HeLa-MaTu-ADR, NCI-H460, DU145, Caco-2, B16F10, A2780 or MOLM-13, compared to the compounds known from prior art.

Another object of the invention is to provide CDK9 kinase inhibitors, which show an improved aqueous solubility compared to the compounds known from prior art.

Another object of the invention is to provide CDK9 kinase inhibitors, which show an improved CaCo-2 permeability and/or an improved CaCo-2 efflux ratio, compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines, such as HeLa, HeLa-MaTu-ADR, NCI-H460, DU145, Caco-2, B16F10, A2780 or MOLM-13, and/or which show an improved aqueous solubility, and/or which show an improved CaCo-2 permeability and/or an improved CaCo-2 efflux ratio and/or which show an increased potency to inhibit CDK9 activity at high ATP concentrations compared to the compounds known from prior art.

The present invention relates to compounds of general formula (I)

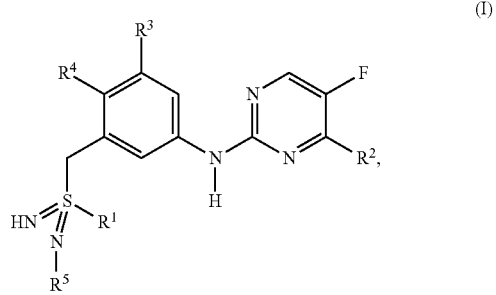

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl, $C_1$-$C_6$- alkoxy, $C_1$-$C_3$-fluoroalkoxy-, —$NH_2$, alkylamino-, dialkylamino-, acetylamino-, N-methyl-N-acetylamino-, cyclic amines, —OP(=O)(OH)$_2$, —C(=O)OH, —C(=O)$NH_2$;

$R^2$ represents a group selected from

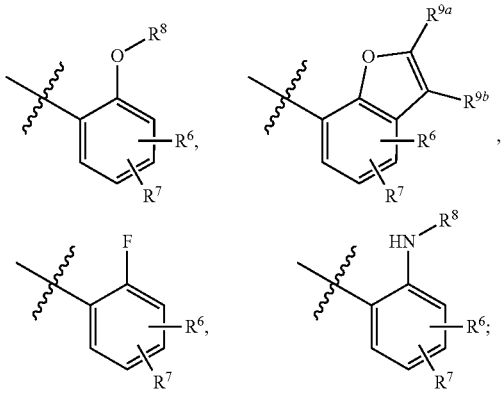

$R^3$ represents a group selected from a fluoro atom, a chloro atom, a bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-;

$R^4$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —S(=O)$_2$$R^{10}$ $C_1$-$C_6$-alkyl-, $C_3$-$C_6$-alkenyl-, $C_3$-$C_6$-alkynyl-, $C_3$-$C_7$-cycloalkyl-, heterocyclyl-, phenyl, heteroaryl, wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
 a) a $C_1$-$C_6$-alkyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one or two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
 b) a phenyl-$C_1$-$C_3$-alkyl- group, the phenyl group of which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
 c) a heteroaryl-$C_1$-$C_3$-alkyl- group, the heteroaryl group of which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
 d) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
 e) a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

$R^{9a}$, $R^{9b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^{10}$ represents a group selected from $C_1$-$C_6$-alkyl-, halo-$C_1$-$C_3$-alkyl-, $C_3$-$C_7$-cycloalkyl-, heterocyclyl-, phenyl, benzyl and heteroaryl,
 wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-,
or the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra(n-butyl) ammonium, or N-benzyl-N,N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen", "halogen atom" or "halo" represents fluorine, chlorine, bromine and iodine, particularly bromine, chlorine or fluorine, preferably chlorine or fluorine, more preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2- dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_6$-alkenyl" is to be understood as preferably meaning a linear or branched, monovalent hydrocarbon group, which contains one double bond, and which has 2, 3, 4, 5 or 6 carbon atoms ("$C_2$-$C_6$-alkenyl"). Particularly, said alkenyl group is a $C_2$-$C_3$-alkenyl, $C_3$-$C_6$-alkenyl or $C_3$-$C_4$-alkenyl group. Said alkenyl group is, for example, a vinyl, allyl, (E)-2-methylvinyl, (Z)-2-methylvinyl or isopropenyl group.

The term "$C_2$-$C_6$-alkynyl" is to be understood as preferably meaning a linear or branched, monovalent hydrocarbon group which contains one triple bond, and which contains 2, 3, 4, 5 or 6 carbon atoms.

Particularly, said alkynyl group is a $C_2$-$C_3$-alkynyl, $C_3$-$C_6$-alkynyl or $C_3$-$C_4$-alkynyl group. Said $C_2$-$C_3$-alkynyl group is, for example, an ethynyl, prop-1-ynyl or prop-2-ynyl group.

The term "$C_3$-$C_7$-cycloalkyl" is to be understood as preferably meaning a saturated or partially unsaturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring is non-aromatic but can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_6$-cycloalkyl group is a monocyclic hydrocarbon ring such as a cyclopropyl, cyclobutyl, cyclopentyl or cyclohexyl group.

The term "$C_3$-$C_6$-cycloalkyl-$C_1$-$C_3$-alkyl-" group is to be understood as preferably meaning a $C_3$-$C_6$-cycloalkyl group as defined supra, in which one of the hydrogen atoms is replaced by a $C_1$-$C_3$-alkyl group, as defined supra, which links the $C_3$-$C_6$-cycloalkyl-$C_1$-$C_3$-alkyl- group to the rest of the molecule. Particularly, said "$C_3$-$C_6$-cycloalkyl-$C_1$-$C_3$-alkyl-" is a "$C_3$-$C_6$-cycloalkyl-$C_1$-$C_2$-alkyl-", preferably it is a "$C_3$-$C_6$-cycloalkyl-methyl-" group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen.

A $C_3$-$C_9$-heterocyclyl is to be understood as meaning a heterocyclyl which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly, a $C_3$-$C_7$-heterocyclyl is to be understood as meaning a heterocyclyl which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly, a $C_3$-$C_6$-heterocyclyl is to be understood as meaning a heterocyclyl which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 8-membered heterocyclic ring"), more particularly said ring can contain 4 or 5 carbon atoms, and 1, 2 or 3 of the above-mentioned heteroatom-containing groups (a "5- to 8-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "heterocyclyl-$C_1$-$C_3$-alkyl-" group is to be understood as preferably meaning a heterocyclyl, preferably a 4- to 7-membered heterocyclic ring, more preferably a 5- to 7-membered heterocyclic ring, each as defined supra, in which one of the hydrogen atoms is replaced by a $C_1$-$C_3$-alkyl group, as defined supra, which links the heterocyclyl-$C_1$-$C_3$-alkyl- group to the rest of the molecule. Particularly, the "heterocyclyl-$C_1$-$C_3$-alkyl-" is a "heterocyclyl-$C_1$-$C_2$-alkyl-", preferably it is a heterocyclyl-methyl-group.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy-, particularly a "$C_1$-$C_2$-fluoroalkoxy" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 or 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-dimethylamino-, N,N-diethylamino-, N-ethyl-N-methylamino-, N-methyl-N-n-propylamino-, N-iso-propyl-N-n-propylamino-, N-tert-butyl-N-methylamino-, N-ethyl-N-n-pentylamino- and N-n-hexyl-N-methylamino-.

The term "cyclic amine" is to be understood as preferably meaning a cyclic amine group. Preferably, a cyclic amine means a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-", or, used synonymously, "$C_1$-$C_3$-haloalkyl-", is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Preferably, a halo-$C_1$-$C_3$-alkyl- group is a fluoro-$C_1$-$C_3$-alkyl- or a fluoro-$C_1$-$C_2$-alkyl- group, such as for example —$CF_3$, —$CHF_2$, —$CH_2F$, —$CF_2CF_3$, or —$CH_2CF_3$, more preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, which links the phenyl-$C_1$-$C_3$-alkyl- group to the rest of the molecule. Particularly, the "phenyl-$C_1$-$C_3$-alkyl-" is a phenyl-$C_1$-$C_2$-alkyl-, preferably it is a benzyl-group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, which links the heteroaryl-$C_1$-$C_3$-alkyl- group to the rest of the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, -a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene) sulfonyloxy, (4-nitro-benzene) sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene) sulfonyloxy, benzenesulfonyloxy, and (4-methoxy-benzene) sulfonyloxy.

As used herein, a chlorinated aliphatic hydrocarbon of the formula chloro-$C_1$-$C_2$-alkyl-H refers to a saturated hydrocarbon consisting of 1 or 2 carbon atoms, 1, 2, 3, 4 or 5 hydrogen atoms and 1, 2, 3, 4 or 5 chloro atoms. Particularly, chloro-$C_1$-$C_2$-alkyl-H refers to dichloromethane, chloroform, or 1,2-dichloroethane, preferably dichloromethane.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_3$, $C_1$-$C_2$, $C_2$-$C_{10}$, $C_2$-$C_9$, $C_2$-$C_8$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_8$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_4$", as used throughout this text, e.g. in the context of the definition of "$C_1$-$C_4$-alkyl", "$C_1$-$C_4$-alkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_1$-$C_3$, $C_1$-$C_2$, $C_2$-$C_4$, $C_2$-$C_3$, $C_3$-$C_4$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$ $C_4$-$C_6$ $C_4$-$C_5$ $C_5$-$C_6$. Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$ $C_5$-$C_6$, $C_6$-$C_7$.

A symbol ⌇ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment, the present invention concerns compounds of general formula (I), wherein
$R^1$ represents a $C_1$-$C_6$-alkyl or $C_3$-$C_5$-cycloalkyl group,
  wherein said group is optionally substituted with one substituent selected from the group consisting of hydroxy, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(=O)(OH)$_2$, —C(=O)OH, —C(=O)NH$_2$;
$R^2$ represents a group selected from

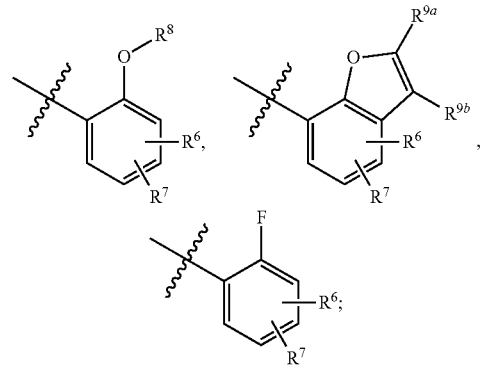

$R^3$ represents a group selected from a fluoro atom, a chloro atom, —$SF_5$, a $C_1$-$C_3$-alkyl and a fluoro-$C_1$-$C_3$-alkyl- group;
$R^4$ represents a hydrogen atom or a fluoro atom;
$R^5$ represents a group selected from a hydrogen atom, cyano, —S(=O)$_2R^{10}$ $C_1$-$C_6$-alkyl-, $C_3$-$C_6$-alkenyl-, $C_3$-$C_6$-alkynyl-, $C_3$-$C_5$-cycloalkyl-, phenyl,
  wherein said $C_1$-$C_6$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-;
$R^6$, $R^7$ represent, independently from each other, a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-;
$R^8$ represents a group selected from
  a) a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-, phenyl,
    wherein said $C_3$-$C_5$-cycloalkyl- or phenyl group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-;
  b) a phenyl-$C_1$-$C_2$-alkyl- group, the phenyl group of which is optionally substituted with one or two or three substituents, identically or differently, selected from the group consisting of halogen, hydroxy, —NH$_2$, alkylamino-, dialkylamino-, cyclic amines, cyano, C$_1$-C$_3$-alkyl-, fluoro-C$_1$-C$_2$-alkyl-, C$_1$-C$_2$-fluoroalkoxy-, C$_1$-C$_3$-alkoxy-;
c) a heteroaryl-C$_1$-C$_2$-alkyl- group, the heteroaryl group of which is optionally substituted with one or two or three substituents, identically or differently, selected from the group consisting of halogen, hydroxy, —NH$_2$, alkylamino-, dialkylamino-, cyclic amines, cyano, C$_1$-C$_3$-alkyl-, fluoro-C$_1$-C$_2$-alkyl-, C$_1$-C$_2$-fluoroalkoxy-, C$_1$-C$_3$-alkoxy-;
d) a C$_3$-C$_6$-cycloalkyl-C$_1$-C$_2$-alkyl- group, the C$_3$-C$_6$-cycloalkyl group of which is optionally substituted with one or two or three substituents, identically or differently, selected from halogen, C$_1$-C$_3$-alkyl-, C$_1$-C$_3$-alkoxy-, fluoro-C$_1$-C$_2$-alkyl-, C$_1$-C$_2$-fluoroalkoxy-;
e) a heterocyclyl-C$_1$-C$_2$-alkyl- group, the heterocyclyl group of which is optionally substituted with one or two or three substituents, identically or differently, selected from halogen, C$_1$-C$_3$-alkyl-, C$_1$-C$_3$-alkoxy-, fluoro-C$_1$-C$_2$-alkyl-, C$_1$-C$_2$-fluoroalkoxy-;

R$^{9a}$, R$^{9b}$ represent, independently from each other, a group selected from a hydrogen atom, a fluoro atom, a chloro atom, a bromo atom, cyano, C$_1$-C$_3$-alkyl-, C$_1$-C$_3$-alkoxy-, fluoro-C$_1$-C$_2$-alkyl-, C$_1$-C$_2$-fluoroalkoxy-;

R$^{10}$ represents a group selected from C$_1$-C$_4$-alkyl-, fluoro-C$_1$-C$_3$-alkyl-, C$_3$-C$_7$-cycloalkyl-, heterocyclyl-, phenyl, benzyl and heteroaryl,
wherein said group is optionally substituted with one, two or three substituents, identically or differently, selected from the group consisting of halogen, hydroxy, C$_1$-C$_3$-alkyl-, C$_1$-C$_3$-alkoxy-, —NH$_2$, alkylamino-, dialkylamino-, cyclic amines, fluoro-C$_1$-C$_2$-alkyl-, C$_1$-C$_2$-fluoroalkoxy-, or the enantiomers, diastereomers, salts, solvates or salts of solvates thereof.

In a preferred embodiment the present invention concerns compounds of general formula (I), wherein
R$^1$ represents a C$_1$-C$_6$-alkyl or C$_3$-C$_5$-cycloalkyl group,
wherein said group is optionally substituted with one substituent selected from the group consisting of hydroxy, C$_1$-C$_3$-alkoxy-, —NH$_2$, alkylamino-, dialkylamino-, cyclic amines, —OP(=O)(OH)$_2$;
R$^2$ represents a group selected from

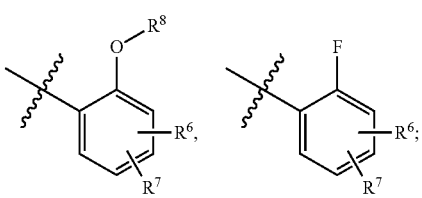

R$^3$ represents a group selected from a fluoro atom, a chloro atom, —SF$_5$, a C$_1$-C$_3$-alkyl and a fluoro-C$_1$-C$_3$-alkyl- group;
R$^4$ represents a hydrogen atom or a fluoro atom;
R$^5$ represents a group selected from a hydrogen atom, cyano, C$_1$-C$_4$-alkyl-, C$_3$-C$_4$-alkynyl-, C$_3$-C$_5$-cycloalkyl-, phenyl, wherein said C$_1$-C$_4$-alkyl, C$_3$-C$_5$-cycloalkyl- or phenyl group is optionally substituted with one, two or three substituents, identically or differently, selected from the group consisting of halogen, hydroxy, cyano, C$_1$-C$_3$-alkyl-, C$_1$-C$_3$-alkoxy-;

R$^6$, R$^7$ represent, independently from each other, a group selected from a hydrogen atom, a fluoro atom and a chloro atom;
R$^8$ represents a group selected from
a) a C$_1$-C$_4$-alkyl group, which is optionally substituted with one or two or three substituents, identically or differently, selected from the group consisting of halogen, hydroxy, —NH$_2$, alkylamino-, dialkylamino-, cyclic amines, cyano, C$_1$-C$_3$-alkyl-, fluoro-C$_1$-C$_2$-alkyl-, C$_1$-C$_2$-fluoroalkoxy-, C$_2$-C$_3$-alkenyl-, C$_2$-C$_3$-alkynyl-, C$_3$-C$_5$-cycloalkyl-;
b) a phenyl-C$_1$-C$_2$-alkyl- group, the phenyl group of which is optionally substituted with one or two or three substituents, identically or differently, selected from the group consisting of halogen, hydroxy, —NH$_2$, alkylamino-, dialkylamino-, cyclic amines, cyano, C$_1$-C$_3$-alkyl-, fluoro-C$_1$-C$_2$-alkyl-, C$_1$-C$_2$-fluoroalkoxy-, C$_1$-C$_3$-alkoxy-;

or the enantiomers, diastereomers, salts, solvates or salts of solvates thereof.

In another preferred embodiment the present invention concerns compounds of general formula (I), wherein
R$^1$ represents a C$_1$-C$_6$-alkyl group,
wherein said group is optionally substituted with one substituent selected from the group consisting of C$_1$-C$_3$-alkoxy-, —NH$_2$, alkylamino-, dialkylamino- and cyclic amines;
R$^2$ represents a group selected from

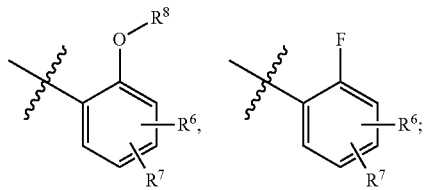

R$^3$ represents a group selected from a fluoro atom, a chloro atom, —SF$_5$, a methyl and a trifluoromethyl- group;
R$^4$ represents a hydrogen atom or a fluoro atom;
R$^5$ represents a group selected from a hydrogen atom, cyano, C$_1$-C$_4$-alkyl-, C$_3$-C$_4$-alkynyl-, phenyl,
wherein said C$_1$-C$_4$-alkyl or phenyl group is optionally substituted with one substituent selected from the group consisting of a fluoro atom, a chloro atom, a bromo atom, hydroxy, cyano, methyl, methoxy-;
R$^6$, R$^7$ represent, independently from each other, a group selected from a hydrogen atom, a fluoro atom and a chloro atom;
R$^8$ represents a group selected from
a) a C$_1$-C$_4$-alkyl group, which is optionally substituted with one substituent selected from the group consisting of hydroxy, —NH$_2$, alkylamino-, dialkylamino-, cyano, C$_1$-C$_2$-alkoxy-, C$_3$-C$_5$-cycloalkyl-;
b) a phenyl-C$_1$-C$_2$-alkyl- group, the phenyl group of which is optionally substituted with one substituent selected from the group consisting of halogen, hydroxy, —NH$_2$, alkylamino-, dialkylamino-, cyano, methyl-, trifluoromethyl-, trifluoromethoxy-, methoxy-;

or the enantiomers, diastereomers, salts, solvates or salts of solvates thereof.

In a particularly preferred embodiment, the present invention concerns compounds of general formula (I), wherein $R^1$ represents a $C_1$-$C_3$-alkyl group;
$R^2$ represents a group selected from

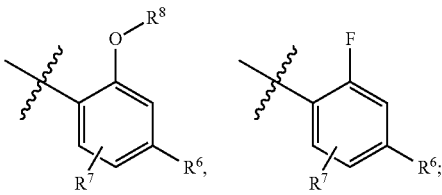

$R^3$ represents a group selected from a fluoro atom, a chloro atom, —$SF_5$ and a trifluoromethyl- group;
$R^4$ represents a hydrogen atom;
$R^5$ represents a group selected from a hydrogen atom, cyano, $C_1$-$C_4$-alkyl-, $C_3$-$C_4$-alkynyl-, phenyl,
wherein said $C_1$-$C_4$-alkyl or phenyl group is optionally substituted with one substituent selected from the group consisting of a fluoro atom, hydroxy, cyano, methyl, methoxy-;
$R^6$ represents a group selected from hydrogen, a fluoro atom and a chloro atom,
$R^7$ represents hydrogen;
$R^8$ represents a $C_1$-$C_3$-alkyl group;
or the enantiomers, diastereomers, salts, solvates or salts of solvates thereof.

In another particularly preferred embodiment, the present invention concerns compounds of general formula (I), wherein $R^1$ represents a $C_1$-$C_3$-alkyl group;
$R^2$ represents a group selected from

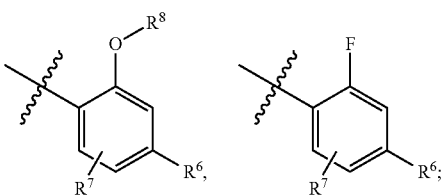

$R^3$ represents a group selected from a fluoro atom and —$SF_5$;
$R^4$ represents a hydrogen atom;
$R^5$ represents a group selected from a hydrogen atom, cyano, $C_1$-$C_3$-alkyl-, prop-2-yn-1-yl-, phenyl,
wherein said $C_1$-$C_3$-alkyl group is optionally substituted with one hydroxy group;
$R^6$ represents a fluoro atom,
$R^7$ represents hydrogen;
$R^8$ represents a $C_1$-$C_3$-alkyl group;
or the enantiomers, diastereomers, salts, solvates or salts of solvates thereof.

In another particularly preferred embodiment, the present invention concerns compounds of general formula (I), wherein
$R^1$ represents a methyl group;
$R^2$ represents a group selected from

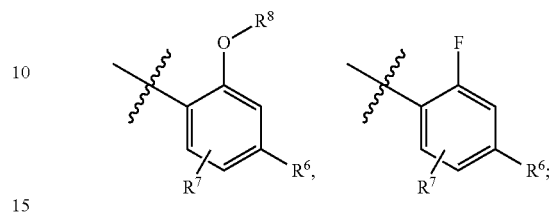

$R^3$ represents a group selected from a fluoro atom and —$SF_5$;
$R^4$ represents a hydrogen atom;
$R^5$ represents a group selected from a hydrogen atom, cyano, methyl, 3-hydroxypropyl-, prop-2-yn-1-yl-, phenyl;
$R^6$ represents a fluoro atom,
$R^7$ represents hydrogen;
$R^8$ represents a methyl group;
or the enantiomers, diastereomers, salts, solvates or salts of solvates thereof.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(=O)(OH)$_2$, —C(=O)OH, —C(=O)NH$_2$.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one substituent selected from the group consisting of hydroxy, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(=O)(OH)$_2$, —C(=O)OH, —C(=O)NH$_2$.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one substituent selected from the group consisting of hydroxy, $C_1$-$C_3$-alkoxy-, —$NH_2$, alkylamino-, dialkylamino-, cyclic amines, —OP(=O)(OH)$_2$.

In another embodiment the invention relates to compounds of formula (I), in which $R^1$ represents a $C_1$-$C_6$-alkyl or $C_3$-$C_5$-cycloalkyl group,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(=O)(OH)$_2$, —C(=O)OH, —C(=O)NH$_2$.

In another embodiment the invention relates to compounds of formula (I), in which R$^1$ represents a C$_1$-C$_6$-alkyl or C$_3$-C$_5$-cycloalkyl group,
wherein said group is optionally substituted with one substituent selected from the group consisting of hydroxy, C$_1$-C$_3$-alkyl-, fluoro-C$_1$-C$_2$-alkyl-, C$_1$-C$_3$-alkoxy-, C$_1$-C$_2$-fluoroalkoxy-, —NH$_2$, alkylamino-, dialkylamino-, cyclic amines, —OP(=O)(OH)$_2$, —C(=O)OH, —C(=O)NH$_2$.

In another embodiment the invention relates to compounds of formula (I), in which R$^1$ represents a C$_1$-C$_6$-alkyl or C$_3$-C$_5$-cycloalkyl group,
wherein said group is optionally substituted with one substituent selected from the group consisting of hydroxy, C$_1$-C$_3$-alkoxy-, —NH$_2$, alkylamino-, dialkylamino-, cyclic amines, —OP(=O)(OH)$_2$.

In another embodiment the invention relates to compounds of formula (I), in which R$^1$ represents a C$_1$-C$_6$-alkyl or C$_3$-C$_5$-cycloalkyl group,
wherein said group is optionally substituted with one substituent selected from the group consisting of C$_1$-C$_3$-alkoxy-, —NH$_2$, alkylamino-, dialkylamino- and cyclic amines.

In a preferred embodiment the invention relates to compounds of formula (I), in which R$^1$ represents a C$_1$-C$_6$-alkyl group,
wherein said group is optionally substituted with one substituent selected from the group consisting of hydroxy, C$_1$-C$_3$-alkyl-, fluoro-C$_1$-C$_2$-alkyl-, C$_1$-C$_3$-alkoxy-, C$_1$-C$_2$-fluoroalkoxy-, —NH$_2$, alkylamino-, dialkylamino-, cyclic amines, —OP(=O)(OH)$_2$, —C(=O)OH, —C(=O)NH$_2$.

In another preferred embodiment the invention relates to compounds of formula (I), in which R$^1$ represents a C$_1$-C$_6$-alkyl group,
wherein said group is optionally substituted with one substituent selected from the group consisting of hydroxy, C$_1$-C$_3$-alkoxy-, —NH$_2$, alkylamino-, dialkylamino-, cyclic amines, —OP(=O)(OH)$_2$.

In another preferred embodiment the invention relates to compounds of formula (I), in which R$^1$ represents a C$_1$-C$_6$-alkyl group,
wherein said group is optionally substituted with one substituent selected from the group consisting of C$_1$-C$_3$-alkoxy-, —NH$_2$, alkylamino-, dialkylamino- and cyclic amines In another preferred embodiment the invention relates to compounds of formula (I), in which R$^1$ represents a C$_1$-C$_3$-alkyl group,
wherein said group is optionally substituted with one substituent selected from the group consisting of C$_1$-C$_3$-alkoxy-, —NH$_2$, alkylamino-, dialkylamino- and cyclic amines.

In a particularly preferred embodiment the invention relates to compounds of formula (I), in which R$^1$ represents a C$_1$-C$_3$-alkyl group.

In another particularly preferred embodiment the invention relates to compounds of formula (I), in which R$^1$ represents a methyl group.

In another particularly preferred embodiment the invention relates to compounds of formula (I), in which R$^1$ represents an ethyl group.

In another particularly preferred embodiment the invention relates to compounds of formula (I), in which R$^1$ represents a n-propyl group.

In another particularly preferred embodiment the invention relates to compounds of formula (I), in which R$^1$ represents an iso-propyl group.

In another embodiment the invention relates to compounds of formula (I), in which R$^2$ represents a group selected from

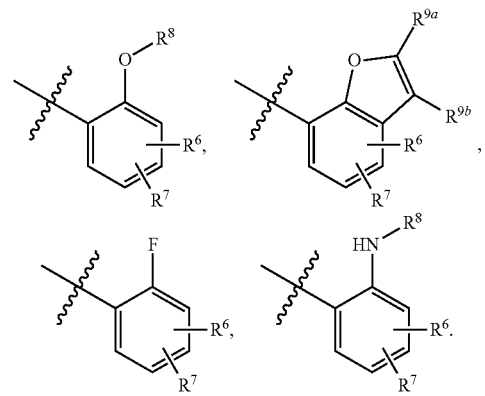

In another embodiment the invention relates to compounds of formula (I), in which R$^2$ represents a group selected from

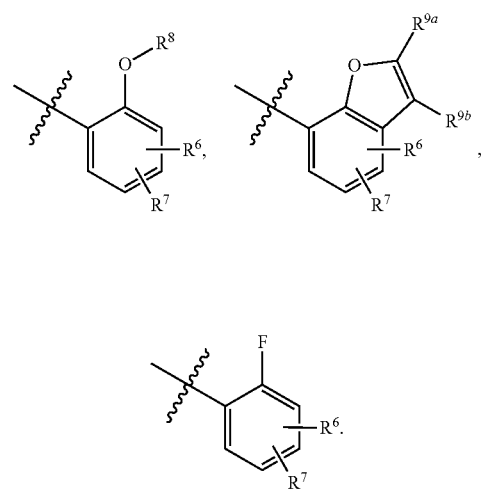

In another embodiment the invention relates to compounds of formula (I), in which R$^2$ represents a group

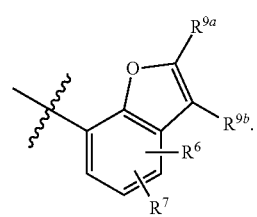

In a preferred embodiment the invention relates to compounds of formula (I), in which $R^2$ represents a group selected from

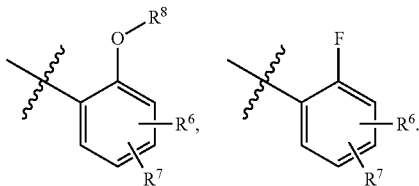

In another preferred embodiment the invention relates to compounds of formula (I), in which $R^2$ represents a group

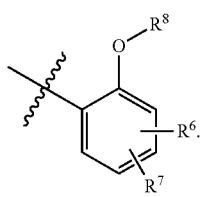

In another preferred embodiment the invention relates to compounds of formula (I), in which $R^2$ represents a group

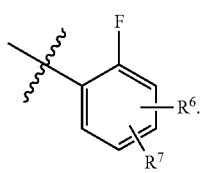

In a particularly preferred embodiment the invention relates to compounds of formula (I), in which $R^2$ represents a group selected from

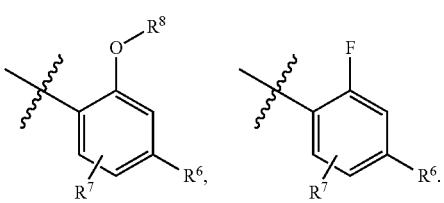

In another particularly preferred embodiment the invention relates to compounds of formula (I), in which $R^2$ represents a group

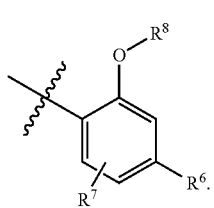

In another particularly preferred embodiment the invention relates to compounds of formula (I), in which $R^2$ represents a group

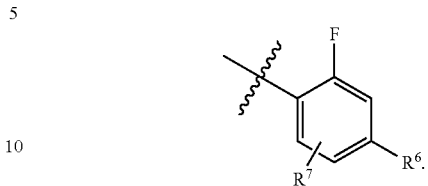

In another particularly preferred embodiment the invention relates to compounds of formula (I), in which $R^2$ represents a group selected from 4-fluoro-2-methoxyphenyl- and 2,4-difluorophenyl-.

In another particularly preferred embodiment the invention relates to compounds of formula (I), in which $R^2$ represents a 4-fluoro-2-methoxyphenyl- group.

In another particularly preferred embodiment the invention relates to compounds of formula (I), in which $R^2$ represents a 2,4-difluorophenyl- group.

In another embodiment the invention relates to compounds of formula (I), in which $R^3$ represents a group selected from a fluoro atom, a chloro atom, a bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a fluoro atom, a chloro atom, a bromo atom, cyano, —$SF_5$, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^3$ represents a group selected from a fluoro atom, a chloro atom, a bromo atom, cyano, —$SF_5$, methyl-, methoxy-, difluoromethyl-, trifluoromethyl-, difluoromethoxy-, trifluoromethoxy-.

In a preferred embodiment the invention relates to compounds of formula (I), in which $R^3$ represents a group selected from a fluoro atom, a chloro atom, —$SF_5$, a $C_1$-$C_3$-alkyl and a fluoro-$C_1$-$C_3$-alkyl- group.

In another preferred embodiment the invention relates to compounds of formula (I), in which $R^3$ represents a group selected from a fluoro atom, a chloro atom, —$SF_5$, a $C_1$-$C_2$-alkyl and a fluoro-$C_1$-$C_2$-alkyl- group.

In another preferred embodiment the invention relates to compounds of formula (I), in which $R^3$ represents a group selected from a fluoro atom, a chloro atom, —$SF_5$, a methyl and a trifluoromethyl- group.

In another preferred embodiment the invention relates to compounds of formula (I), in which $R^3$ represents a group selected from a fluoro atom, —$SF_5$, a methyl and a trifluoromethyl- group.

In a particularly preferred embodiment the invention relates to compounds of formula (I), in which $R^3$ represents a group selected from a fluoro atom, a chloro atom, —$SF_5$, and a trifluoromethyl- group.

In another particularly preferred embodiment the invention relates to compounds of formula (I), in which $R^3$ represents a group selected from a fluoro atom, —$SF_5$, and a trifluoromethyl- group.

In another particularly preferred embodiment the invention relates to compounds of formula (I), in which $R^3$ represents a group selected from a fluoro atom and —$SF_5$.

In another particularly preferred embodiment the invention relates to compounds of formula (I), in which $R^3$ represents a fluoro atom.

In another particularly preferred embodiment the invention relates to compounds of formula (I), in which $R^3$ represents a —$SF_5$ group.

In another embodiment the invention relates to compounds of formula (I), in which $R^4$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^4$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In a preferred embodiment the invention relates to compounds of formula (I), in which $R^4$ represents a group selected from a hydrogen atom, a fluoro atom, a chloro atom, a methyl and a trifluoromethyl- group.

In another preferred embodiment the invention relates to compounds of formula (I), in which $R^4$ represents a group selected from a hydrogen atom, a fluoro atom and a chloro atom.

In a particularly preferred embodiment the invention relates to compounds of formula (I), in which $R^4$ represents a group selected from a hydrogen atom and a fluoro atom.

In another particularly preferred embodiment the invention relates to compounds of formula (I), in which $R^4$ represents a fluoro atom.

In another particularly preferred embodiment the invention relates to compounds of formula (I), in which $R^4$ represents a hydrogen atom.

In another embodiment the invention relates to compounds of formula (I), in which $R^3$ represents a group selected from a fluoro atom, a chloro atom, a bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-, and in which $R^4$ represents a group selected from a hydrogen atom and a fluoro atom.

In another embodiment the invention relates to compounds of formula (I), in which $R^3$ represents a group selected from a fluoro atom, a chloro atom, a bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-, and in which $R^4$ represents a hydrogen atom.

In another embodiment the invention relates to compounds of formula (I), in which $R^3$ represents a group selected from a fluoro atom, a chloro atom, a bromo atom, cyano, —$SF_5$, $C_1$-$C_2$-alkyl-, fluoro-$C_1$-$C_2$-alkyl-, $C_1$-$C_2$-fluoroalkoxy-, and in which $R^4$ represents a group selected from a hydrogen atom and a fluoro atom.

In another embodiment the invention relates to compounds of formula (I), in which $R^3$ represents a group selected from a fluoro atom, a chloro atom, a bromo atom, cyano, —$SF_5$, $C_1$-$C_2$-alkyl-, fluoro-$C_1$-$C_2$-alkyl-, $C_1$-$C_2$-fluoroalkoxy-, and in which $R^4$ represents a hydrogen atom.

In another embodiment the invention relates to compounds of formula (I), in which $R^3$ represents a group selected from a fluoro atom, a chloro atom, a bromo atom, cyano, —$SF_5$, methyl-, methoxy-, difluoromethyl-, trifluoromethyl-, difluoromethoxy-, trifluoromethoxy-, and in which $R^4$ represents a group selected from a hydrogen atom and a fluoro atom.

In another embodiment the invention relates to compounds of formula (I), in which $R^3$ represents a group selected from a fluoro atom, a chloro atom, a bromo atom, cyano, —$SF_5$, methyl-, methoxy-, difluoromethyl-, trifluoromethyl-, difluoromethoxy-, trifluoromethoxy-, and in which $R^4$ represents a hydrogen atom.

In a preferred embodiment the invention relates to compounds of formula (I), in which $R^3$ represents a group selected from a fluoro atom, a chloro atom, —$SF_5$, a $C_1$-$C_3$-alkyl and a fluoro-$C_1$-$C_3$-alkyl- group, and in which $R^4$ represents a group selected from a hydrogen atom and a fluoro atom.

In a preferred embodiment the invention relates to compounds of formula (I), in which $R^3$ represents a group selected from a fluoro atom, a chloro atom, —$SF_5$, a $C_1$-$C_3$-alkyl and a fluoro-$C_1$-$C_3$-alkyl- group, and in which $R^4$ represents a hydrogen atom.

In another preferred embodiment the invention relates to compounds of formula (I), in which $R^3$ represents a group selected from a fluoro atom, a chloro atom, —$SF_5$, a $C_1$-$C_2$-alkyl and a fluoro-$C_1$-$C_2$-alkyl- group, and in which $R^4$ represents a group selected from a hydrogen atom and a fluoro atom.

In another preferred embodiment the invention relates to compounds of formula (I), in which $R^3$ represents a group selected from a fluoro atom, a chloro atom, —$SF_5$, a $C_1$-$C_2$-alkyl and a fluoro-$C_1$-$C_2$-alkyl- group, and in which $R^4$ represents a hydrogen atom.

In another preferred embodiment the invention relates to compounds of formula (I), in which $R^3$ represents a group selected from a fluoro atom, a chloro atom, —$SF_5$, a methyl and a trifluoromethyl- group, and in which $R^4$ represents a group selected from a hydrogen atom and a fluoro atom.

In another preferred embodiment the invention relates to compounds of formula (I), in which $R^3$ represents a group selected from a fluoro atom, a chloro atom, —$SF_5$, a methyl and a trifluoromethyl- group, and in which $R^4$ represents a hydrogen atom.

In another preferred embodiment the invention relates to compounds of formula (I), in which $R^3$ represents a group selected from a fluoro atom, —$SF_5$, a methyl and a trifluoromethyl- group, and in which $R^4$ represents a group selected from a hydrogen atom and a fluoro atom.

In another preferred embodiment the invention relates to compounds of formula (I), in which $R^3$ represents a group selected from a fluoro atom, —$SF_5$, a methyl and a trifluoromethyl- group, and in which $R^4$ represents a hydrogen atom.

In a particularly preferred embodiment the invention relates to compounds of formula (I), in which $R^3$ represents a group selected from a fluoro atom, a chloro atom, —$SF_5$, and a trifluoromethyl- group, and in which $R^4$ represents a group selected from a hydrogen atom and a fluoro atom.

In a particularly preferred embodiment the invention relates to compounds of formula (I), in which $R^3$ represents a group selected from a fluoro atom, a chloro atom, —$SF_5$, and a trifluoromethyl- group, and in which $R^4$ represents a hydrogen atom.

In another particularly preferred embodiment the invention relates to compounds of formula (I), in which $R^3$ represents a group selected from a fluoro atom, —$SF_5$, and a trifluoromethyl- group, and in which $R^4$ represents a group selected from a hydrogen atom and a fluoro atom.

In another particularly preferred embodiment the invention relates to compounds of formula (I), in which $R^3$ represents a group selected from a fluoro atom, —$SF_5$, and a trifluoromethyl- group, and in which $R^4$ represents a hydrogen atom.

In another particularly preferred embodiment the invention relates to compounds of formula (I), in which $R^3$ represents a group selected from a fluoro atom and —$SF_5$, and in which $R^4$ represents a group selected from a hydrogen atom and a fluoro atom.

In another particularly preferred embodiment the invention relates to compounds of formula (I), in which $R^3$ represents a group selected from a fluoro atom and —$SF_5$ and in which $R^4$ represents a hydrogen atom.

In another particularly preferred embodiment the invention relates to compounds of formula (I), in which $R^3$ represents a group selected from a fluoro atom and —$SF_5$ and in which $R^4$ represents a fluoro atom.

In another particularly preferred embodiment the invention relates to compounds of formula (I), in which $R^3$ represents a fluoro atom, and in which $R^4$ represents a group selected from a hydrogen atom and a fluoro atom.

In another particularly preferred embodiment the invention relates to compounds of formula (I), in which $R^3$ represents a fluoro atom, and in which $R^4$ represents a hydrogen atom.

In another particularly preferred embodiment the invention relates to compounds of formula (I), in which $R^3$ represents a fluoro atom, and in which $R^4$ represents a fluoro atom.

In another particularly preferred embodiment the invention relates to compounds of formula (I), in which $R^3$ represents a —$SF_5$ group, and in which $R^4$ represents a group selected from a hydrogen atom and a fluoro atom.

In another particularly preferred embodiment the invention relates to compounds of formula (I), in which $R^3$ represents a —$SF_5$ group, and in which $R^4$ represents a hydrogen atom.

In another particularly preferred embodiment the invention relates to compounds of formula (I), in which $R^3$ represents a —$SF_5$ group, and in which $R^4$ represents a fluoro atom.

In another embodiment the invention relates to compounds of formula (I), in which $R^5$ represents a group selected from a hydrogen atom, cyano, —$S(=O)_2R^{10}$, $C_1$-$C_6$-alkyl-, $C_3$-$C_6$-alkenyl-, $C_3$-$C_6$-alkynyl-, $C_3$-$C_7$-cycloalkyl-, heterocyclyl-, phenyl, heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —$S(=O)_2R^{10}$, $C_1$-$C_6$-alkyl-, $C_3$-$C_6$-alkenyl-, $C_3$-$C_6$-alkynyl-, $C_3$-$C_7$-cycloalkyl-, heterocyclyl-, phenyl, heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In another embodiment the invention relates to compounds of formula (I), in which $R^5$ represents a group selected from a hydrogen atom, cyano, —$S(=O)_2R^{10}$, $C_1$-$C_6$-alkyl-, $C_3$-$C_6$-alkenyl-, $C_3$-$C_6$-alkynyl-, $C_3$-$C_5$-cycloalkyl-, phenyl, heteroaryl,
wherein said $C_1$-$C_6$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —$S(=O)_2R^{10}$, $C_1$-$C_6$-alkyl-, $C_3$-$C_6$-alkenyl-, $C_3$-$C_6$-alkynyl-, $C_3$-$C_5$-cycloalkyl-, phenyl,
wherein said $C_1$-$C_6$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In another embodiment the invention relates to compounds of formula (I), in which $R^5$ represents a group selected from a hydrogen atom, cyano, —$S(=O)_2R^{10}$, $C_1$-$C_6$-alkyl-, $C_3$-$C_6$-alkenyl-, $C_3$-$C_6$-alkynyl-, $C_3$-$C_5$-cycloalkyl-, phenyl,
wherein said $C_1$-$C_6$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-.

In another embodiment the invention relates to compounds of formula (I), in which $R^5$ represents a group selected from a hydrogen atom, cyano, $C_1$-$C_4$-alkyl-, $C_3$-$C_4$-alkynyl-, $C_3$-$C_5$-cycloalkyl-, phenyl,
wherein said $C_1$-$C_4$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In a preferred embodiment the invention relates to compounds of formula (I), in which $R^5$ represents a group selected from a hydrogen atom, $C_1$-$C_4$-alkyl-, $C_3$-$C_4$-alkynyl-, $C_3$-$C_5$-cycloalkyl-, phenyl,
wherein said $C_1$-$C_4$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-.

In another preferred embodiment the invention relates to compounds of formula (I), in which $R^5$ represents a group selected from a hydrogen atom, cyano, $C_1$-$C_4$-alkyl-, $C_3$-$C_4$-alkynyl-, $C_3$-$C_5$-cycloalkyl-, phenyl,
  wherein said $C_1$-$C_4$-alkyl, $C_3$-$C_5$-cycloalkyl- or phenyl is optionally substituted with one substituent selected from the group consisting of a fluoro atom, a chloro atom, a bromo atom, hydroxy, cyano, methyl, methoxy-.

In a preferred embodiment the invention relates to compounds of formula (I), in which $R^5$ represents a group selected from a hydrogen atom, cyano, $C_1$-$C_4$-alkyl-, $C_3$-$C_4$-alkynyl-, phenyl,
  wherein said $C_1$-$C_4$-alkyl or phenyl group is optionally substituted with one, two or three substituents, identically or differently, selected from the group consisting of halogen, hydroxy, cyano, $C_1$-$C_3$-alkyl-, $C_1$-$C_3$-alkoxy-.

In another preferred embodiment the invention relates to compounds of formula (I), in which $R^5$ represents a group selected from a hydrogen atom, cyano, $C_1$-$C_4$-alkyl-, $C_3$-$C_4$-alkynyl-, phenyl,
  wherein said $C_1$-$C_4$-alkyl or phenyl group is optionally substituted with one substituent selected from the group consisting of a fluoro atom, a chloro atom, a bromo atom, hydroxy, cyano, methyl, methoxy-.

In a particularly preferred embodiment the invention relates to compounds of formula (I), in which $R^5$ represents a group selected from a hydrogen atom, cyano, $C_1$-$C_4$-alkyl-, $C_3$-$C_4$-alkynyl-, phenyl,
  wherein said $C_1$-$C_4$-alkyl or phenyl group is optionally substituted with one substituent selected from the group consisting of a fluoro atom, hydroxy, cyano, methyl, methoxy-.

In another particularly preferred embodiment the invention relates to compounds of formula (I), in which $R^5$ represents a group selected from a hydrogen atom, cyano, $C_1$-$C_3$-alkyl-, prop-2-yn-1-yl-, phenyl,
  wherein said $C_1$-$C_3$-alkyl group is optionally substituted with one hydroxy group.

In another particularly preferred embodiment the invention relates to compounds of formula (I), in which $R^5$ represents a group selected from a hydrogen atom, cyano, $C_1$-$C_3$-alkyl-, phenyl,
  wherein said $C_1$-$C_3$-alkyl group is optionally substituted with one hydroxy group.

In another particularly preferred embodiment the invention relates to compounds of formula (I), in which $R^5$ represents a $C_1$-$C_3$-alkyl- group,
  wherein said $C_1$-$C_3$-alkyl group is optionally substituted with one hydroxy group.

In another particularly preferred embodiment the invention relates to compounds of formula (I), in which $R^5$ represents a hydrogen atom.

In another particularly preferred embodiment the invention relates to compounds of formula (I), in which $R^5$ represents a cyano group.

In another particularly preferred embodiment the invention relates to compounds of formula (I), in which $R^5$ represents a phenyl group.

In another particularly preferred embodiment the invention relates to compounds of formula (I), in which $R^5$ represents a prop-2-yn-1-yl- group.

In another particularly preferred embodiment the invention relates to compounds of formula (I), in which $R^5$ represents a group selected from a hydrogen atom, cyano, methyl, 3-hydroxypropyl-, prop-2-yn-1-yl-, phenyl.

In another particularly preferred embodiment the invention relates to compounds of formula (I), in which $R^5$ represents a methyl group.

In another particularly preferred embodiment the invention relates to compounds of formula (I), in which $R^5$ represents an ethyl group.

In another particularly preferred embodiment the invention relates to compounds of formula (I), in which $R^5$ represents a 3-hydroxypropyl group.

In another embodiment the invention relates to compounds of formula (I), in which $R^6$ and $R^7$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from hydrogen, a fluoro atom, a chloro atom, a bromo atom, cyano, $C_1$-$C_3$-alkyl-, $C_1$-$C_3$-alkoxy-, fluoro-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from hydrogen, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^6$ and $R^7$ represent, independently from each other, hydrogen, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ and $R^7$ represent, independently from each other, a hydrogen atom, a fluoro atom, a chloro atom, a bromo atom, cyano or methyl-.

In another embodiment the invention relates to compounds of formula (I), in which $R^6$ and $R^7$ represent, independently from each other, a hydrogen atom, a fluoro atom, a chloro atom, a bromo atom or cyano.

In a preferred embodiment the invention relates to compounds of formula (I), in which $R^6$ and $R^7$ represent, independently from each other, a hydrogen atom, a fluoro atom or a chloro atom.

In another preferred embodiment the invention relates to compounds of formula (I), in which $R^6$ and $R^7$ represent, independently from each other, a hydrogen atom or a fluoro atom.

In another embodiment the invention relates to compounds of formula (I), in which $R^6$ represents a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl, $C_1$-$C_2$-fluoroalkoxy-, and $R^7$ represents a hydrogen atom, a fluoro atom or a chloro atom.

In another embodiment the invention relates to compounds of formula (I), in which $R^6$ represents a hydrogen atom, a fluoro atom or a chloro atom, and $R^7$ represents a group selected from a hydrogen atom, a fluoro atom or a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^6$ represents a hydrogen atom, a fluoro atom, a chloro atom, a bromo atom, cyano, methyl-, methoxy-, difluoromethyl-, trifluoromethyl-, difluoromethoxy-, trifluoromethoxy-, and $R^7$ represents a hydrogen atom, a fluoro atom or a chloro atom.

In another embodiment the invention relates to compounds of formula (I), in which $R^6$ represents a hydrogen atom, a fluoro atom or a chloro atom, and $R^7$ represents a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ represents a hydrogen atom, a fluoro atom, a chloro atom, a bromo atom, cyano or methyl-, and $R^7$ represents a hydrogen atom or a fluoro atom.

In another embodiment the invention relates to compounds of formula (I), in which $R^6$ represents a hydrogen atom or a fluoro atom, a chloro atom, and $R^7$ represents a hydrogen atom, a fluoro atom, a chloro atom a bromo atom, cyano or methyl-.

In another embodiment the invention relates to compounds of formula (I), in which $R^6$ represents a hydrogen atom, a fluoro atom, a chloro atom, a bromo atom or cyano, and $R^7$ represents a hydrogen atom or a fluoro atom.

In another embodiment the invention relates to compounds of formula (I), in which $R^6$ represents a hydrogen atom or a fluoro atom, and $R^7$ represents a hydrogen atom, a fluoro atom, a chloro atom a bromo atom or cyano.

In a preferred embodiment the invention relates to compounds of formula (I), in which $R^6$ represents a hydrogen atom, a fluoro atom or a chloro atom, and $R^7$ represents a hydrogen atom or a fluoro atom.

In another preferred embodiment the invention relates to compounds of formula (I), in which $R^6$ represents a hydrogen atom or a fluoro atom, and $R^7$ represents a hydrogen atom, a fluoro atom or a chloro atom.

In another preferred embodiment the invention relates to compounds of formula (I), in which $R^6$ represents a hydrogen atom or a fluoro atom, and $R^7$ represents a hydrogen atom.

In another preferred embodiment the invention relates to compounds of formula (I), in which $R^6$ represents a hydrogen atom, and $R^7$ represents a hydrogen atom or a fluoro atom.

In another preferred embodiment the invention relates to compounds of formula (I), in which $R^6$ represents hydrogen, para-fluoro, or para-chloro, whereby para refers to the point of attachment of $R^2$ to the rest of the molecule, and in which $R^7$ represents a hydrogen atom.

In another preferred embodiment the invention relates to compounds of formula (I), in which $R^6$ represents para-fluoro, whereby para refers to the point of attachment of $R^2$ to the rest of the molecule, and in which $R^7$ represents a hydrogen atom.

In another preferred embodiment the invention relates to compounds of formula (I), in which $R^6$ and $R^7$ represent a hydrogen atom.

In another preferred embodiment the invention relates to compounds of formula (I), in which $R^6$ and $R^7$ represent a fluoro atom.

In another embodiment the invention relates to compounds of formula (I), in which $R^6$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ represents a hydrogen atom, a fluoro atom, a chloro atom, a bromo atom or cyano.

In another embodiment the invention relates to compounds of formula (I), in which $R^6$ represents a hydrogen atom, a fluoro atom, a chloro atom or a bromo atom.

In another embodiment the invention relates to compounds of formula (I), in which $R^6$ represents a hydrogen atom, a fluoro atom or a chloro atom.

In a preferred embodiment the invention relates to compounds of formula (I), in which $R^6$ represents a hydrogen atom or a fluoro atom.

In another preferred embodiment the invention relates to compounds of formula (I), in which $R^6$ represents a hydrogen atom.

In another preferred embodiment the invention relates to compounds of formula (I), in which $R^6$ represents a fluoro atom.

In another preferred embodiment the invention relates to compounds of formula (I), in which $R^6$ represents para-fluoro, whereby para refers to the point of attachment of $R^2$ to the rest of the molecule.

In another embodiment the invention relates to compounds of formula (I), in which $R^7$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^7$ represents a hydrogen atom, a fluoro atom, a chloro atom, a bromo atom or cyano.

In another embodiment the invention relates to compounds of formula (I), in which $R^7$ represents a hydrogen atom, a fluoro atom, a chloro atom or a bromo atom.

In another embodiment the invention relates to compounds of formula (I), in which $R^7$ represents a hydrogen atom, a fluoro atom or a chloro atom.

In a preferred embodiment the invention relates to compounds of formula (I), in which $R^7$ represents a hydrogen atom or a fluoro atom.

In another preferred embodiment the invention relates to compounds of formula (I), in which $R^7$ represents a hydrogen atom.

In another preferred embodiment the invention relates to compounds of formula (I), in which $R^7$ represents a fluoro atom.

In another embodiment the invention relates to compounds of formula (I), in which $R^8$ represents a group selected from
a) a $C_1$-$C_6$-alkyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
b) a phenyl-$C_1$-$C_3$-alkyl- group, the phenyl group of which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
c) a heteroaryl-$C_1$-$C_3$-alkyl- group, the heteroaryl group of which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
- d) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
- e) a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a group selected from
- a) a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-, phenyl, wherein said $C_3$-$C_5$-cycloalkyl- or phenyl group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-;
- b) a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-;
- c) a heteroaryl-$C_1$-$C_2$-alkyl- group, the heteroaryl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-;
- d) a $C_3$-$C_6$-cycloalkyl-$C_1$-$C_2$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, fluoro-$C_1$-$C_2$-alkyl-, $C_1$-$C_2$-fluoroalkoxy-;
- e) a heterocyclyl-$C_1$-$C_2$-alkyl- group, the heterocyclyl group of which is optionally substituted with one or two or three substituents, identically or differently, selected from halogen, $C_1$-$C_3$-alkyl-, $C_1$-$C_3$-alkoxy-, fluoro-$C_1$-$C_2$-alkyl-, $C_1$-$C_2$-fluoroalkoxy-.

In another embodiment the invention relates to compounds of formula (I), in which $R^8$ represents a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-, phenyl, wherein said $C_3$-$C_5$-cycloalkyl- or phenyl group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In another embodiment the invention relates to compounds of formula (I), in which $R^8$ represents a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-.

In another embodiment the invention relates to compounds of formula (I), in which $R^8$ represents a heteroaryl-$C_1$-$C_2$-alkyl- group, the heteroaryl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-.

In another embodiment the invention relates to compounds of formula (I), in which $R^8$ represents a $C_3$-$C_6$-cycloalkyl-$C_1$-$C_2$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, fluoro-$C_1$-$C_2$-alkyl-, $C_1$-$C_2$-fluoroalkoxy-.

In another embodiment the invention relates to compounds of formula (I), in which $R^8$ represents a heterocyclyl-$C_1$-$C_2$-alkyl- group, the heterocyclyl group of which is optionally substituted with one or two or three substituents, identically or differently, selected from halogen, $C_1$-$C_3$-alkyl-, $C_1$-$C_3$-alkoxy-, fluoro-$C_1$-$C_2$-alkyl-, $C_1$-$C_2$-fluoroalkoxy-.

In a preferred embodiment the invention relates to compounds of formula (I), in which $R^8$ represents a group selected from
- a) a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-;
- b) a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-.

In another preferred embodiment the invention relates to compounds of formula (I), in which $R^8$ represents a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-.

In another preferred embodiment the invention relates to compounds of formula (I), in which $R^8$ represents a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-.

In another preferred embodiment the invention relates to compounds of formula (I), in which $R^8$ represents a group selected from
a) a $C_1$-$C_4$-alkyl group, which is optionally substituted with one substituent selected from the group consisting of hydroxy, —$NH_2$, alkylamino-, dialkylamino-, cyano, $C_1$-$C_2$-alkoxy-, $C_3$-$C_5$-cycloalkyl-;
b) a phenyl-$C_1$-$C_2$-alkyl- group, the phenyl group of which is optionally substituted with one substituent selected from the group consisting of halogen, hydroxy, —$NH_2$, alkylamino-, dialkylamino-, cyano, methyl-, trifluoromethyl-, trifluoromethoxy-, methoxy-.

In another preferred embodiment the invention relates to compounds of formula (I), in which $R^8$ represents a $C_1$-$C_4$-alkyl group, which is optionally substituted with one substituent selected from the group consisting of hydroxy, —$NH_2$, alkylamino-, dialkylamino-, cyano, $C_1$-$C_2$-alkoxy-, $C_3$-$C_5$-cycloalkyl-.

In another preferred embodiment the invention relates to compounds of formula (I), in which $R^8$ represents a phenyl-$C_1$-$C_2$-alkyl- group, the phenyl group of which is optionally substituted with one substituent selected from the group consisting of halogen, hydroxy, —$NH_2$, alkylamino-, dialkylamino-, cyano, methyl-, trifluoromethyl-, trifluoromethoxy-, methoxy-.

In another preferred embodiment the invention relates to compounds of formula (I), in which $R^8$ represents a benzyl group, the phenyl group of which is optionally substituted with one substituent selected from the group consisting of halogen, hydroxy, —$NH_2$, alkylamino-, dialkylamino-, cyano, methyl-, trifluoromethyl-, trifluoromethoxy-, methoxy-.

In another preferred embodiment the invention relates to compounds of formula (I), in which $R^8$ represents a benzyl group, the phenyl group of which is optionally substituted with one substituent selected from the group consisting of a fluoro atom, a chloro atom, a bromo atom, dimethylamino-, cyano, methyl-, trifluoromethyl-, trifluoromethoxy-, methoxy-.

In another preferred embodiment the invention relates to compounds of formula (I), in which $R^8$ represents a benzyl group.

In a particularly preferred embodiment the invention relates to compounds of formula (I), in which $R^8$ represents a $C_1$-$C_3$-alkyl group.

In another particularly preferred embodiment the invention relates to compounds of formula (I), in which $R^8$ represents a methyl group.

In another particularly preferred embodiment the invention relates to compounds of formula (I), in which $R^8$ represents an ethyl group.

In another particularly preferred embodiment the invention relates to compounds of formula (I), in which $R^8$ represents a n-propyl group.

In another particularly preferred embodiment the invention relates to compounds of formula (I), in which $R^8$ represents an iso-propyl group.

In another embodiment the invention relates to compounds of formula (I), in which $R^{9a}$ and $R^{9b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^{9a}$ and $R^{9b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, fluoro-$C_1$-$C_2$-alkyl-, $C_1$-$C_2$-fluoroalkoxy-.

In another embodiment the invention relates to compounds of formula (I), in which $R^{9a}$ and $R^{9b}$ represent, independently from each other, a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^{9a}$ and $R^{9b}$ represent, independently from each other, a hydrogen atom, a fluoro atom, a chloro atom, methyl-, methoxy or trifluoromethyl-.

In another embodiment the invention relates to compounds of formula (I), in which $R^{9a}$ and $R^{9b}$ represent, independently from each other, a hydrogen atom, a fluoro atom or methyl-.

In another embodiment the invention relates to compounds of formula (I), in which $R^{9a}$ and $R^{9b}$ represent, independently from each other, a hydrogen atom or a fluoro atom.

In another embodiment the invention relates to compounds of formula (I), in which $R^{9a}$ and $R^{9b}$ represent, independently from each other, a hydrogen atom or methyl-.

In another embodiment the invention relates to compounds of formula (I), in which $R^{9a}$ represents a hydrogen atom, a fluoro atom, a chloro atom, a bromo atom, cyano, methyl-, methoxy-, difluoromethyl-, trifluoromethyl-, difluoromethoxy-, trifluoromethoxy-, and $R^{9b}$ represents a hydrogen atom or a fluoro atom.

In another embodiment the invention relates to compounds of formula (I), in which $R^{9a}$ represents a hydrogen atom or a fluoro atom, and $R^{9b}$ represents a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^{9a}$ represents a hydrogen atom or a fluoro atom, and $R^{9b}$ represents a hydrogen atom, a fluoro atom, a chloro atom, methyl-, methoxy or trifluoromethyl-.

In another embodiment the invention relates to compounds of formula (I), in which $R^{9a}$ represents a hydrogen atom, a fluoro atom, a chloro atom, methyl-, methoxy or trifluoromethyl-, and $R^{9b}$ represents a hydrogen atom or a fluoro atom.

In another embodiment the invention relates to compounds of formula (I), in which $R^{9a}$ represents a hydrogen atom, and $R^{9b}$ represents a hydrogen atom, a fluoro atom, a chloro atom, methyl-, methoxy or trifluoromethyl-.

In another embodiment the invention relates to compounds of formula (I), in which $R^{9a}$ represents a hydrogen atom, a fluoro atom, a chloro atom, methyl-, methoxy or trifluoromethyl-, and $R^{9b}$ represents a hydrogen atom.

In another embodiment the invention relates to compounds of formula (I), in which $R^{9a}$ represents a hydrogen atom, and $R^{9b}$ represents a hydrogen atom, a fluoro atom or methyl-.

In another embodiment the invention relates to compounds of formula (I), in which $R^{9a}$ represents a hydrogen atom, a fluoro atom or methyl-, and $R^{9b}$ represents a hydrogen atom.

In another embodiment the invention relates to compounds of formula (I), in which $R^{9a}$ represents a hydrogen atom, and $R^{9b}$ represents a hydrogen atom or a fluoro atom.

In another embodiment the invention relates to compounds of formula (I), in which $R^{9a}$ represents a hydrogen atom or a fluoro atom, and $R^{9b}$ represents a hydrogen atom.

In another embodiment the invention relates to compounds of formula (I), in which $R^{9a}$ and $R^{9b}$ represent a hydrogen atom.

In another embodiment the invention relates to compounds of formula (I), in which $R^{10}$ represents a group selected from $C_1$-$C_6$-alkyl-, halo-$C_1$-$C_3$-alkyl-, $C_3$-$C_7$-cycloalkyl-, heterocyclyl-, phenyl, benzyl and heteroaryl,
wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^{10}$ represents a group selected from $C_1$-$C_4$-alkyl-, fluoro-$C_1$-$C_3$-alkyl-, $C_3$-$C_7$-cycloalkyl-, heterocyclyl-, phenyl, benzyl and heteroaryl,
wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In another embodiment the invention relates to compounds of formula (I), in which $R^{10}$ represents a group selected from $C_1$-$C_4$-alkyl-, $C_3$-$C_7$-cycloalkyl-, phenyl and benzyl,
wherein said group is optionally substituted with one, two or three substituents, identically or differently, selected from the group consisting of a fluoro atom, a chloro atom, a bromo atom, hydroxy, $C_1$-$C_2$-alkyl-, $C_1$-$C_2$-alkoxy-, —$NH_2$, methylamino-, dimethylamino-, trifluoromethyl-, trifluoromethoxy-.

In another embodiment the invention relates to compounds of formula (I), in which $R^{10}$ represents a group selected from $C_1$-$C_4$-alkyl-, $C_5$-$C_6$-cycloalkyl-, phenyl and benzyl,
wherein said group is optionally substituted with one substituent selected from the group consisting of a fluoro atom, hydroxy, methyl-, methoxy-, —$NH_2$, methylamino-, dimethylamino-, trifluoromethyl-.

In another embodiment the invention relates to compounds of formula (I), in which $R^{10}$ represents a $C_1$-$C_3$-alkyl group.

It is to be understood that the present invention relates to any sub-combination within any embodiment of the present invention of compounds of formula (I), supra.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds:
5-Fluoro-4-(4-fluoro-2-methoxyphenyl)-N-{3-fluoro-5-[(S-methylsulfonodiimidoyl)methyl]phenyl}pyrimidin-2-amine;
(rac)-N-{3-[(N,S-Dimethylsulfonodiimidoyl)methyl]-5-fluorophenyl}-5-fluoro-4-(4-fluoro-2-methoxyphenyl) pyrimidin-2-amine;
(rac)-5-Fluoro-4-(4-fluoro-2-methoxyphenyl)-N-{3-fluoro-5-[(S-methyl-N-phenylsulfonodiimidoyl)methyl] phenyl}pyrimidin-2-amine;
(rac)-5-Fluoro-4-(4-fluoro-2-methoxyphenyl)-N-(3-fluoro-5-{[S-methyl-N-(prop-2-yn-1-yl)sulfonodiimidoyl] methyl}phenyl)pyrimidin-2-amine;
(rac)-[(3-Fluoro-5-{[5-fluoro-4-(4-fluoro-2-methoxyphenyl)pyrimidin-2-yl]amino}benzyl)(imino)methyl-$\lambda^6$-sulfanylidene]cyanamide;
(rac)-3-{[(3-Fluoro-5-{[5-fluoro-4-(4-fluoro-2-methoxyphenyl)pyrimidin-2-yl]amino}benzyl)(imino)methyl-$\lambda^6$-sulfanylidene]amino}propan-1-ol;
4-(2,4-Difluorophenyl)-5-fluoro-N-{3-[(S-methylsulfonodiimidoyl)methyl]-5-(pentafluoro-$\lambda^6$-sulfanyl) phenyl}pyrimidin-2-amine;
5-Fluoro-4-(4-fluoro-2-methoxyphenyl)-N-{3-[(S-methylsulfonodiimidoyl)methyl]-5-(pentafluoro-$\lambda^6$-sulfanyl) phenyl}pyrimidin-2-amine,
or the enantiomers, diastereomers, salts, solvates or salts of solvates thereof.

The above mentioned definitions of radicals which have been detailed in general terms or in preferred ranges also apply to the end products of the formula (I) and, analogously, to the starting materials or intermediates required in each case for the preparation.

The present invention further relates to a process for the preparation of the compounds of formula (I), in which process compounds of formula (6),

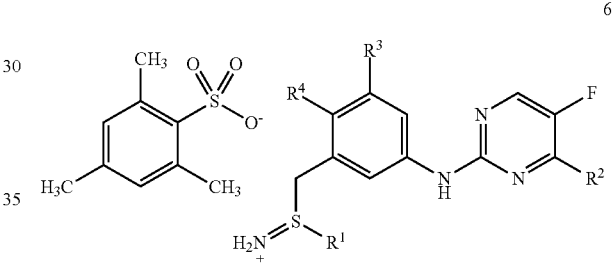

6 in which $R^1$, $R^2$, $R^3$ and $R^4$ are as as defined for the compound of formula (I) according to the invention, are oxidised by treatment with N-chloro succinimide, in N,N-dimethylformamide (DMF), N,N-dimethylacetamide or N-methylpyrrolidin-2-one, or a mixture thereof, as a solvent, in the presence of an alkali carbonate,
followed by the addition of an amine of the formula $R^5$—$NH_2$, in which $R^5$ is defined as for the compound of formula (I) according to the invention, to give compounds of the formula (I),

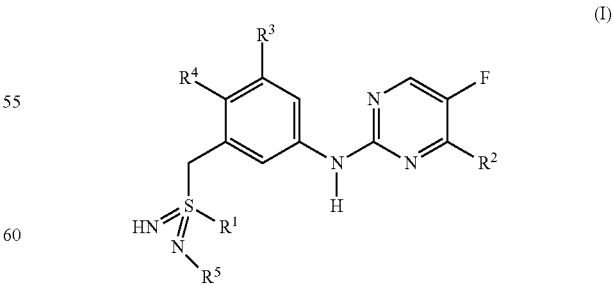

(I)

and in which process the resulting compounds are optionally, if appropriate, converted with the corresponding (i) solvents and/or (ii) bases or acids to the solvates, salts and/or solvates of the salts thereof.

The present invention further relates to a process for the preparation of the compounds of formula (Ia), in which $R^1$, $R^2$, $R^3$ and $R^4$ are as as defined for the compound of formula (I) according to the invention, in which process compounds of formula (6),

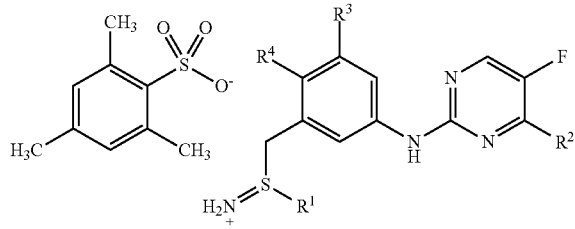

6 in which $R^1$, $R^2$, $R^3$ and $R^4$ are as as defined for the compound of formula (I) according to the invention, are oxidised by treatment with N-chloro succinimide, in N,N-dimethylformamide (DMF), N,N-dimethylacetamide or N-methylpyrrolidin-2-one, or a mixture thereof, as a solvent, in the presence of an alkali carbonate, followed by the addition of hexamethyldisilazene, to give compounds of the formula (Ia),

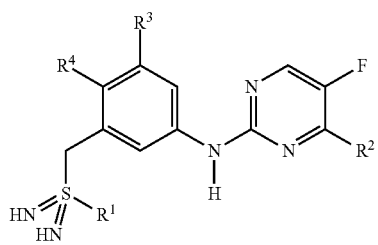

(Ia)

and in which process the resulting compounds are optionally, if appropriate, converted with the corresponding (i) solvents and/or (ii) bases or acids to the solvates, salts and/or solvates of the salts thereof.

The invention furthermore relates to a process for the preparation of the compounds of formula (6), in which process compounds of the formula (5), in which $R^1$, $R^2$, $R^3$ and $R^4$ are as defined for the compound of formula (I) according to the invention,

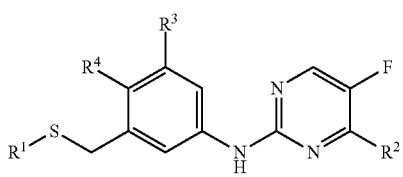

5 are reacted with O-mesitylenesulfonyl hydroxylamine, in a chlorinated aliphatic hydrocarbon of the formula chloro-$C_1$-$C_2$-alkyl-H,

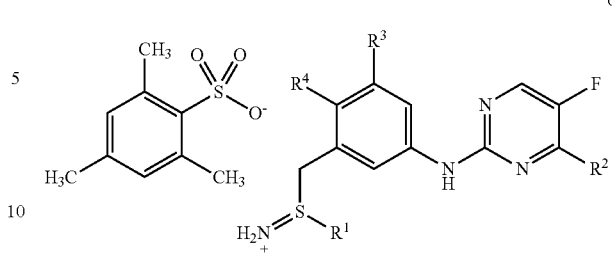

6 to give compounds of the formula (6), in which $R^1$, $R^2$, $R^3$ and $R^4$ are as as defined for the compound of formula (I) according to the invention.

The invention further relates to compounds of the formula (6), in which $R^1$, $R^2$, $R^3$ and $R^4$ are as as defined for the compound of formula (I) according to the invention,

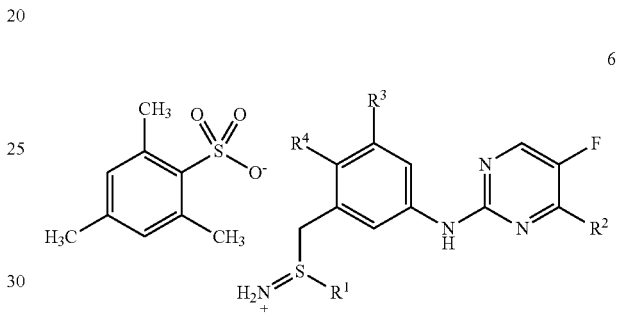

6 or the enantiomers, diastereomers, and solvates thereof.

The invention further relates to the use of the compounds of the formula (6), in which $R^1$, $R^2$, $R^3$ and $R^4$ are as as defined for the compound of formula (I) according to the invention,

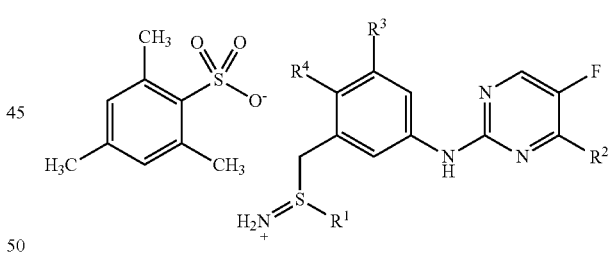

6 or the enantiomers, diastereomers, and solvates thereof,
for the preparation of compounds of the formula (I).

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as the enantiomers, diastereomers, salts, solvates and salts of solvates thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as the enantiomers, diastereomers, salts, solvates and salts of solvates thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2a. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Compounds of the present invention according to general formula (I) show a significantly stronger CDK9 inhibition at high ATP concentrations as compared to CDK2 inhibition at high ATP concentration.

In context of the present invention, the $IC_{50}$ value with respect to CDK2 at high ATP concentration can be determined by the methods described in the method section below. Preferably, it is determined according to Method 2b. ("CDK2/CycE high ATP kinase assay") described in the Materials and Method section below.

Further, preferred compounds of the present invention according to formula (I) show an improved anti-proliferative activity in tumor cell lines, such as HeLa, HeLa-MaTu-ADR, NCI-H460, DU145, Caco-2, B16F10, A2780 or MOLM-13, compared to the CDK9 inhibitors described in the prior art. In context of the present invention, the anti-proliferative activity in tumor cell lines such as HeLa, HeLa-MaTu-ADR, NCI-H460, DU145, Caco-2, B16F10, A2780 or MOLM-13 is preferably determined according to Method 3. ("Proliferation Assay") as described in the Materials and Method section below.

Further, preferred compounds of the present invention according to formula (I) surprisingly show an increased solubility in water at pH 6.5 compared to the compounds described in the prior art.

In context of the present invention the solubility in water at pH 6.5 is preferably determined according to Equilibrium Shake Flask Solubility Assays, Method 4a. ("High Throughput determination of aqueous drug solubility (100 mmolar in DMSO)") and Method 4b. ("Thermodynamic solubility in water from powder"), described in the Materials and Method section below.

Further, preferred compounds of the present invention according to formula (I) are characterized by improved pharmacokinetic properties, such as an increased apparent Caco-2 permeability ($P_{app}$ A–B) across Caco-2 cell monolayers, compared to the compounds known from the prior art.

Further, preferred compounds of the present invention according to formula (I) are characterized by improved pharmacokinetic properties, such as a decreased efflux ratio (efflux ratio=$P_{app}$ B–A/$P_{app}$ A–B) from the basal to apical compartment across Caco-2 cell monolayers, compared to the compounds known from the prior art.

In context of the present invention, the apparent Caco-2 permeability values from the basal to apical compartment ($P_{app}$ A–B) or the efflux ratio (defined as the ratio (($P_{app}$ B–A)/($P_{app}$ A–B)) are preferably determined according to Method 5. ("Caco-2 Permeation Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals"

includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, anal gland adenocarcinomas, and mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip and oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention as a medicament.

A further subject matter of the present invention is the use of the compounds of general formula (I) according to the invention for the treatment and/or prophylaxis of disorders, in particular of the disorders mentioned above.

A preferred subject matter of the present invention is the use of the compounds of general formula (I) according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use as a medicament.

A further subject matter of the present invention are the compounds according to the invention for the treatment and/or prophylaxis of the disorders mentioned above.

A preferred subject matter of the present invention are the compounds according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use in a method for the treatment and/or prophylaxis of the disorders mentioned above.

A preferred subject matter of the present invention are the compounds according to the invention for the use in a method of treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias using an effective amount of the compounds according to the invention.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Another aspect of the present invention relates to the use of the pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Another aspect of the present invention relates to pharmaceutical combinations and/or the pharmaceutical compositions according to the invention for the treatment and/or prophylaxis of disorders, in particular of the disorders mentioned above.

Another aspect of the present invention relates to pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Compounds of formula (I) may be administered as the sole pharmaceutical agent or in combination with one or more additional therapeutic agents where the combination causes no unacceptable adverse effects.

This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2a. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2b. CDK2/CycE High ATP Kinase Assay:

CDK2/CycE-inhibitory activity of compounds of the present invention at 2 mM adenosine-tri-phosphate (ATP) was quantified employing the CDK2/CycE TR-FRET (TR- FRET=Time Resolved Fluorescence Energy Transfer) assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution ATP (3.33 mM=>final conc. in the 5 µl assay volume is 2 mM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 15 ng/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

Non-adherent MOLM-13 human acute myeloid leukemia cells (DSMZ ACC 554) were seeded at a density of 5,000 cells/well in a 96-well multititer plate in 100 µL of growth medium supplemented 10% fetal calf serum. After 24 hours, cell viability of one plate (zero-point plate) was determined with the Cell Titre-Glo Luminescent Cell Viability Assay (Promega), while 50 µL of test compound containing medium was added to the wells of the other plates (final concentrations in the range of 0.001-10 µM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Equilibrium Shake Flask Solubility Assays:

4a) High Throughput Determination of Aqueous Drug Solubility (100 mmolar in DMSO)

The high throughput screening method to determine aqueous drug solubility is based on:

Thomas Onofrey and Greg Kazan, Performance and correlation of a 96-well high throughput screening method to determine aqueous drug solubility, http://www.millipore.com/publications.nsf/a73664f9f981af8c852569b9005b4eee/e565516fb76e7435852 56da30052db77/$FILE/AN1731EN00.pdf The assay was run in a 96-well plate format. Each well was filled with an individual compound.

All pipetting steps were performed using a robot platform.

100 µl of a 10 mmolar solution of drug in DMSO were concentrated by vacuum centrifugation and resolved in 10 µl DMSO. 990 µl phosphate buffer pH 6.5 were added. The content of DMSO amounts to 1%. The multititer plate was put on a shaker and mixed for 24 hrs at room temperature. 150 µl of the suspension were transferred to a filtration plate. After filtration using a vacuum manifold the filtrate was diluted 1:400 and 1:8000. A second microtiter plate with 20 µl of a 10 mM solution of drug in DMSO served for calibration. Two concentrations (0.005 µM and 0.0025 µM) were prepared by dilution in DMSO/water 1:1 and used for calibration. Filtrate and calibration plates were quantified by HPLC-MS/MS.

Chemicals:

Preparation of 0.1 m Phosphate Buffer pH 6.5:

61.86 g NaCl and 39.54 mg $KH_2PO_4$ were solved in water and filled up to 1 l. The mixture was diluted 1:10 with water and the pH adjusted to 6.5 by NaOH.

Materials:

Millipore MultiScreen$_{HTS}$-HV Plate 0.45 µm

Chromatographic conditions were as follows:
HPLC column: Ascentis Express C18 2.7 µm 4.6×30 mm
Injection volume: 1 µl
Flow: 1.5 ml/min
Mobile phase: acidic gradient
   A: Water/0.05% HCOOH
   B: Acetonitrile/0.05% HCOOH
   0 min→95% A 5% B
   0.75 min→5% A 95% B
   2.75 min→5% A 95% B
   2.76 min→95% A 5% B
   3 min→95% A 5% B The areas of sample- and calibration injections were determined by using mass spectrometry software (AB SCIEX: Discovery Quant 2.1.3. and Analyst 1.6.1). The calculation of the solubility value (in mg/l) was executed by an inhouse developed Excel macro.

4b) Thermodynamic Solubility in Water from Powder

The thermodynamic solubility of compounds in water was determined by an equilibrium shake flask method (see for example: E. H. Kerns, L. Di: Drug-like Properties: Concepts, Structure Design and Methods, 276-286, Burlington, Mass., Academic Press, 2008). A saturated solution of the drug was prepared and the solution was mixed for 24 h to ensure that equilibrium was reached. The solution was centrifuged to remove the insoluble fraction and the concentration of the compound in solution was determined using a standard calibration curve. To prepare the sample, 2 mg solid compound was weighed in a 4 mL glass vial. 1 mL phosphate buffer pH 6.5 was added. The suspension was stirred for 24 hrs at room temperature. The solution was centrifuged afterwards. To prepare the sample for the standard calibration, 2 mg solid sample was dissolved in 30 mL acetonitrile. After sonification the solution was diluted with water to 50 mL. Sample and standards were quantified by HPLC with UV-detection. For each sample two injection volumes (5 and 50 µl) in triplicates were made. Three injection volumes (5 µl, 10 µl and 20 µl) were made for the standard.

Chromatographic conditions:
HPLC column: Xterra MS C18 2.5 µm 4.6×30 mm
Injection volume: Sample: 3×5 µl and 3×50 µl
   Standard: 5 µl, 10 µl, 20 µl
Flow: 1.5 mL/min
Mobile phase: acidic gradient:
   A: Water/0.01% TFA
   B: Acetonitrile/0.01% TFA
   0 min→95% A 5% B
   0-3 min→35% A 65% B, linear gradient
   3-5 min→35% A 65% B, isocratic
   5-6 min→95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

4c) Thermodynamic Solubility in Citrate Buffer pH 4

Thermodynamic solubility was determined by an equilibrium shake flask method [Literature: Edward H. Kerns and Li Di (2008) Solubility Methods in: Drug-like Properties: Concepts, Structure Design and Methods, p 276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 1.5 mg solid compound was weighed in a 4 ml glass vial. 1 ml Citrate buffer pH 4 was added. The suspension was put on a stirrer and mixed for 24 hrs at room temperature. The solution was centrifuged afterwards. To prepare the sample for the standard calibration, 0.6 mg solid sample was dissolved in 19 ml acetonitrile/water 1:1. After sonification the solution was filled up with acetonitrile/water 1:1 to 20 ml.

Sample and standards were quantified by HPLC with UV-detection. For each sample two injection volumes (5 and 50 µl) in triplicates were made. Three injection volumes (5 µl, 10 µl and 20 µl) were made for the standard.

Chemicals:

Citrate buffer pH 4 (MERCK Art. 109435; 1 L buffer consisting of 11,768 g citric acid, 4,480 g sodium hydroxide, 1,604 g hydrogen chloride)

Chromatographic conditions were as follows:
HPLC column: Xterra MS C18 2.5 µm 4.6×30 mm
Injection volume: Sample: 3×5 µl and 3×50 µl
   Standard: 5 µl, 10 µl, 20 µl
Flow: 1.5 ml/min
Mobile phase: acidic gradient:
   A: Water/0.01% TFA
   B: Acetonitrile/0.01% TFA
   0 min: 95% A 5% B
   0-3 min: 35% A 65% B, linear gradient
   3-5 min: 35% A 65% B, isocratic
   5-6 min: 95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

The areas of sample- and standard injections as well as the calculation of the solubility value (in mg/l) were determined by using HPLC software (Waters Empower 2 FR).

5. Caco-2 Permeation Assay:

Caco-2 cells (purchased from DSMZ Braunschweig, Germany) were seeded at a density of $4.5 \times 10^4$ cells per well on 24 well insert plates, 0.4 μm pore size, and grown for 15 days in DMEM medium supplemented with 10% fetal bovine serum, 1% GlutaMAX (100×, GIBCO), 100 U/mL penicillin, 100 μg/mL streptomycin (GIBCO) and 1% non essential amino acids (100×). Cells were maintained at 37° C. in a humidified 5% $CO_2$ atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 μM in transport buffer. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp=(Vr/P0)(1/S)(P2/t)$$

Where Vr is the volume of medium in the receiver chamber, P0 is the measured peak area or height of the test drug in the donor chamber at t=0, S the surface area of the monolayer, P2 is the measured peak area of the test drug in the acceptor chamber after 2 h of incubation, and t is the incubation time. The efflux ratio basolateral (B) to apical (A) was calculated by dividing the Papp B–A by the Papp A–B. In addition the compound recovery was calculated.

PREPARATIVE EXAMPLES

Syntheses of Compounds

The syntheses of the sulfondiimine derivatives of formula (I) according to the present invention are preferably carried out according to the general synthetic sequences as shown in Scheme 1.

In addition to said routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents $R^2$, $R^3$, $R^4$ and/or $R^5$ can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, 4$^{th}$ edition, Wiley 2006). Specific examples are described in the subsequent paragraphs. Further, it is possible that two or more successive steps may be performed without work-up being performed between said steps, e.g. a "one-pot" reaction, as it is well-known to a person skilled in the art.

The geometry of the sulfondiimine moiety renders some of the compounds of the general formula (I) chiral. Separation of racemic sulfondiimines into their enantiomers can be achieved by methods known to the person skilled in the art, preferably by means of preparative HPLC on chiral stationary phase.

In the first step 2,4-dichloro-5-fluoropyrimidine (1; CAS-No. 2927-71-1) is reacted with a boronic acid derivative $R^2$—B(OR)$_2$ of formula (2), in which $R^2$ is as defined for the compound of general formula (I), to give a compound of formula (3). The boronic acid derivative (2) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—). For a review see: D. G. Hall, Boronic Acids, 2005 WILEY-VCH Verlag GmbH & Co. KGaA, Weinheim, ISBN 3-527-30991-8 and references cited therein.

The coupling reaction is catalyzed by Pd catalysts, e.g. by Pd(0) catalysts like tetrakis(triphenylphosphine)palladium (0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$].

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

In the second step, a compound of formula (3) is reacted with an aniline derivative of formula (4), in which $R^1$, $R^3$ and $R^4$ are as defined for the compound of general formula (I), to give the corresponding cross-coupling product of formula (5). The compounds of formula (5) can be prepared by Palladium-catalyzed C—N cross-coupling reactions (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the use of suitable palladium precatalysts based upon biarylmonophosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propyl-1,1'-biphenyl) [2-(2-aminoethyl)phenyl]palladium(II) methyl-tert-butylether adduct, 2-dicyclohexylphosphino-2',4',6'-triisopropyl-biphenyl and potassium phosphate in toluene and 1-methylpyrrolidin-2-one. The reactions are preferably run under an atmosphere of argon for 3 hours at 130° C. in a microwave oven or in an oil bath.

Alternatively, this coupling reaction can be carried out in an alcohol such as 1-butanol or in an inert solvent such as DMF, THF, DME, dioxane or mixtures of such solvents in the presence of an acid such as trifluoroacetic acid, hydrogen chloride or 4-methylbenzenesulfonic acid. Preferably, the reaction is carried out at elevated temperatures, for example 140° C.

Aniline derivatives of formula (4) can be prepared by methods known to the person skilled in the art, e.g. by reduction of the corresponding nitrobenzene derivatives. The thioether moiety present in aniline derivatives of formula (4), or the respective nitrobenzene precursors, can be readily introduced by reaction of the corresponding benzylic halides with thiols of formula R¹SH, in which R¹ is as defined for the compound of formula (I), under basic conditions. Thiols of formula R¹—SH are known to the person skilled in the art and are commercially available in considerable variety.

Scheme 1

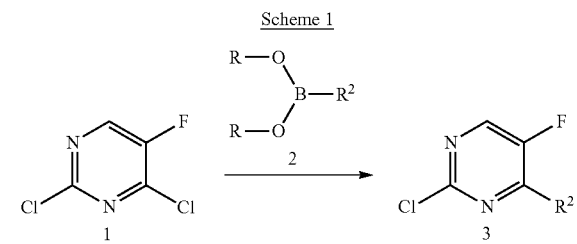

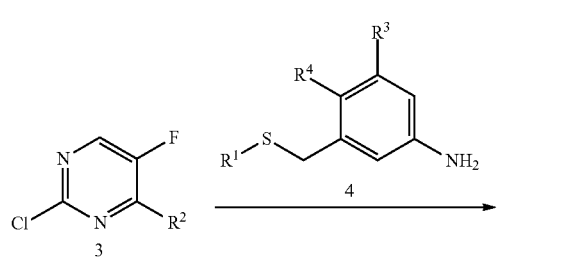

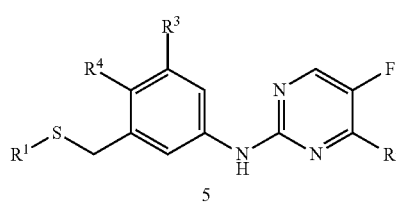

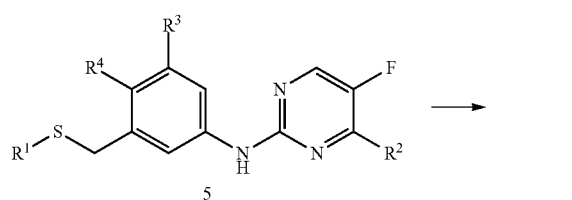

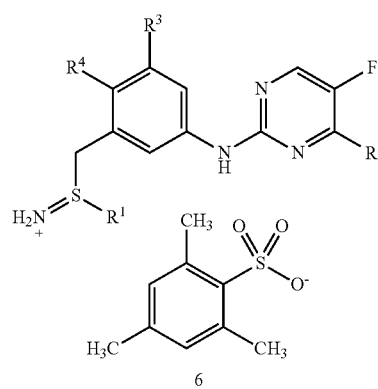

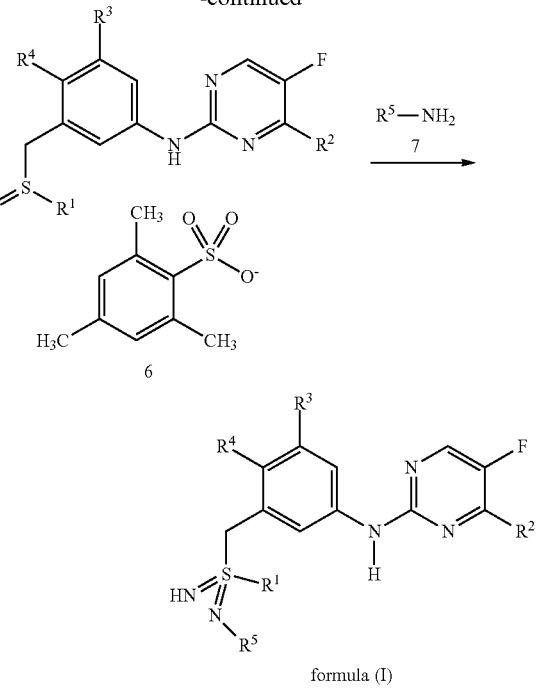

formula (I)

In the third step, a sulfide of formula (5) is converted to a compound of formula (6), by treatment with O-mesitylenesulfonyl hydroxylamine (MSH), in an inert solvent, such as a chlorinated aliphatic hydrocarbon of the formula chloro-$C_1$-$C_2$-alkyl-H, more preferably dichloromethane, at a temperature between −20° C. and 80° C., preferably between −10° C. and 60° C., more preferably between 0° C. and 40° C. (see for example: C. Bolm et al, Angew. Chem. 2012, 124, 4516).

In the final step, a compound of formula (6) is converted to a compound of formula (I) in a one-pot sequence by oxidation with N-chlorosuccinimide (NCS), in a carboxamide as a solvent, preferably N,N-dimethylformamide (DMF), N,N-dimethylacetamide or N-methylpyrrolidin-2-one or a mixture thereof, more preferably N,N-dimethylformamide (DMF), in the presence of an alkali carbonate, preferably sodium carbonate as a base, followed by the addition of a primary amine of the formula (7), wherein $R^5$ is as defined for the compound of general formula (I), or hexamethyldisilazane in case $R^5$ in the reaction product represents a hydrogen atom, at a temperature between −20° C. and 50° C., preferably between −10° C. and 40° C., more preferably between 0° C. and 30° C. (see for example: C. Bolm et al, Angew. Chem. 2012, 124, 4516).

An alternative synthesis approach to disubstituted 5-fluoro pyrimidine derivatives containing a sulfondiimine group according to the present invention is described in scheme 2.

In the first step, a compound of formula (3), in which $R^2$ is as defined for the compound of general formula (I), is reacted with a suitable aniline of formula (8), in which $R^3$ and $R^4$ are as defined for the compound of general formula (I), to give a compound of formula (9).

This coupling reaction can be carried out in an alcohol such as 1-butanol or in an inert solvent such as DMF, THF, DME, dioxane or mixtures of such solvents in the presence of an acid such as trifluoroacetic acid, hydrogen chloride or 4-methylbenzenesulfonic acid. Preferably, the reaction is carried out at elevated temperatures, for example 140° C.

Alternatively, Palladium-catalyzed C—N cross-coupling reactions as described above can be employed.

Anilines of formula (8) are commercially available in certain cases, or can be prepared by methods known to the person skilled in the art, e.g. by reduction of the corresponding carboxylic acids or esters thereof.

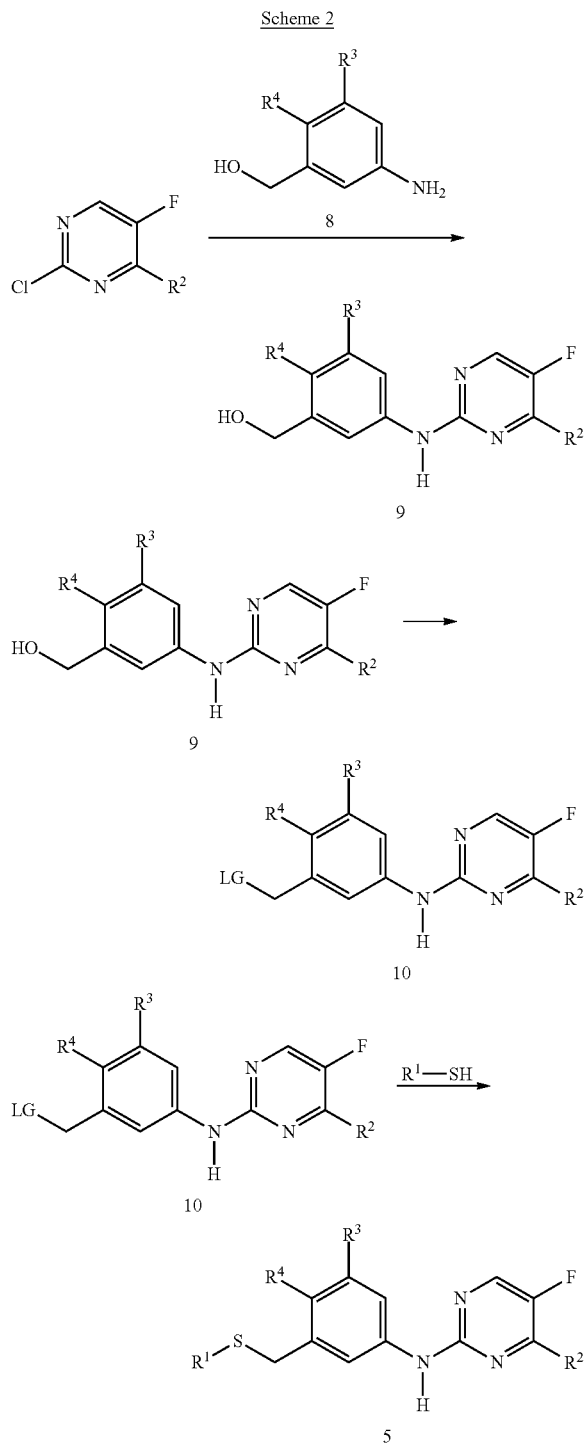

Scheme 2

In the second step, a compound of formula (9), in which $R^2$, $R^3$ and $R^4$ are as defined for the compound of general formula (I), is converted to a compound of formula (10), in which $R^2$, $R^3$ and $R^4$ are as defined for the compound of general formula (I), and in which LG represents a leaving group, preferably chloro or bromo. Preferably and as described herein, thionyl chloride in NMP or DMF and DCM is used for the formation of benzyl chloride derivatives (LG=Cl). A possibility for the formation of benzyl bromide derivatives (LG=Br) is the use of tetrabromomethane and triphenylphosphane in DCM (see for example: Polla et al, Bioorganic and Medicinal Chemistry, 2004, 12, 1151).

In the third step, a compound of formula (10) is converted to a thioether of formula (5), in which $R^1$, $R^2$, $R^3$ and $R^4$ are as defined for the compound of general formula (I), by reaction with suitable thiol of formula $R^1SH$, in which $R^1$ is as defined for the compound of formula (I), under basic conditions, yielding the corresponding thioether of formula (5) (see for example: Sammond et al, Bioorg. Med. Chem. Lett. 2005, 15, 3519). Thiols of formula $R^1$—SH are known to the person skilled in the art and are commercially available in considerable variety.

In the final steps, the thioether of formula (5) can be converted to the corresponding sulfondiimine of formula (I) as described in Scheme 1.

Abbreviations Used in the Description of the Chemistry and in the Examples that Follow are:

br (broad); CDCl$_3$ (deuterated chloroform); cHex (cyclohexane); d (doublet); dd (doublet of doublets); dtr (doublet of triplets); DCM (dichloromethane); DIPEA (di-iso-propylethylamine); DME (1,2-dimethoxyethane), DMF (N,N-dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); MSH (O-Mesitylenesulfonylhydroxylamine); NMP (N-Methylpyrrolidin-2-one); NCS (N-chlorosuccinimide), NMR (nuclear magnetic resonance); p (pentet); Pd(dppf)Cl$_2$ ([1,1'-bis(diphenylphosphino)ferrocene]dichloro palladium(II) complex with dichloromethane); q (quartet); RT (room temperature); s (singlet); sat. aq. (saturated aqueous); SiO$_2$ (silica gel); TFA (trifluoroacetic acid); TFAA (trifluoroacetic anhydride), THF (tetrahydrofuran); tr (triplet); trd (triplet of doublets).

Chemical Naming:

The IUPAC names of the examples were generated using the program 'ACD/Name batch version 12.01' from ACD LABS.

Salt Stoichiometry:

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "xHCl", "xCF$_3$COOH", "xNa$^+$", for example, are to be understood as not a stoichiometric specification, but solely as a salt form.

Example 1

5-Fluoro-4-(4-fluoro-2-methoxyphenyl)-N-{3-fluoro-5-[(S-methylsulfonodiimidoyl)methyl]phenyl}pyrimidin-2-amine (LUEK 4561-3; BAY 1456924)

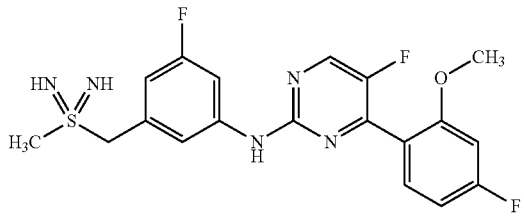 [SMILES: COc1cc(F)ccc1-c1nc(Nc2cc(F)cc(CS(C)(=N)=N)c2)ncc1F]

Preparation of Intermediate 1.1

1-Fluoro-3-[(methylsulfanyl)methyl]-5-nitrobenzene (LUEK 3404-11; BAY 1142659)

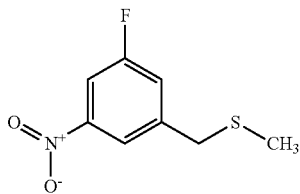

Sodium methanethiolate (5.2 g; 73.8 mmol) was added in three portions to a stirred solution of 1-(chloromethyl)-3-fluoro-5-nitrobenzene (10.0 g; 52.8 mmol; CAS-RN: 1214344-25-8; Hansa Fine Chemicals) in ethanol (108 mL) at 0° C. The cold bath was removed and the batch was stirred at room temperature for 20 hours. The batch was diluted with saturated aqueous sodium chloride solution and extracted two times with ethyl acetate. The combined organic phases were washed with water, dried (sodium sulfate), filtered and concentrated to give the desired product (10.3 g) that was used without further purification.

$^1$H NMR (400 MHz, CDCl$_3$, 300K) δ=8.00 (m, 1H), 7.82 (m, 1H), 7.42 (m, 1H), 3.74 (s, 2H), 2.03 (s, 3H).

Preparation of Intermediate 1.2

3-Fluoro-5-[(methylsulfanyl)methyl]aniline (LUEK 3663-7; BAY 1174741)

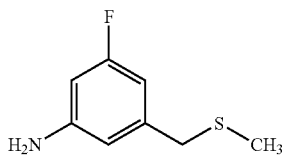

Titanium(III)chloride solution (approx. 15% in approx. 10% hydrochloric acid, 348 mL; Merck Schuchardt OHG) was added to a stirred solution of crude 1-fluoro-3-[(methylsulfanyl)methyl]-5-nitrobenzene (10.3 g) in THF (515 mL) at 0° C. The ice bath was removed and the batch was stirred for 18 hours at room temperature. By adding solid sodium bicarbonate solution the pH value of the reaction mixture, which was cooled with an ice bath, was raised to 7. The batch was saturated with solid sodium chloride and extracted three times with ethyl acetate/THF (1:1). The combined organic phases were washed with saturated aqueous sodium chloride solution, dried (sodium sulfate), filtered and concentrated to give the desired product (7.4 g) that was used without further purification.

$^1$H NMR (400 MHz, CDCl$_3$, 300K) δ=6.41 (m, 2H), 6.26 (m, 1H), 3.55 (s, 2H), 2.01 (s, 3H).

Preparation of Intermediate 1.3

2-Chloro-5-fluoro-4-(4-fluoro-2-methoxyphenyl)pyrimidine

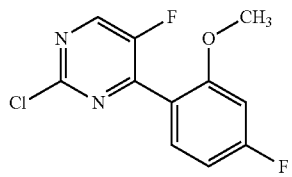 [SMILES: COc1cc(F)ccc1-c1nc(Cl)ncc1F]

A batch with 2,4-dichloro-5-fluoropyrimidine (200 mg; 1.20 mmol; Aldrich Chemical Company Inc.), (4-fluoro-2-methoxyphenyl)boronic acid (224 mg; 1.31 mmol; Aldrich Chemical Company Inc.) and tetrakis(triphenylphosphin)palladium(0) (138 mg; 0.12 mmol) in 1,2-dimethoxyethane (3.6 ml) and 2M solution of potassium carbonate (1.8 ml) was degassed using argon. The batch was stirred under an atmosphere of argon for 16 hours at 90° C. After cooling the batch was diluted with ethyl acetate and washed with saturated aqueous sodium chloride solution. The organic phase was filtered using a Whatman filter and concentrated. The residue was purified by column chromatography on silica gel (hexane/ethyl acetate 1:1) to give the desired product (106 mg; 0.41 mmol).

$^1$H NMR (400 MHz, CDCl$_3$, 300K) δ=8.47 (m, 1H), 7.51 (m, 1H), 6.82 (m, 1H), 6.73 (m, 1H), 3.85 (s, 3H).

Preparation of Intermediate 1.4

5-Fluoro-4-(4-fluoro-2-methoxyphenyl)-N-{3-fluoro-5-[(methylsulfanyl)methyl]phenyl}pyrimidin-2-amine (LUEK 3862-12; BAY 1191376)

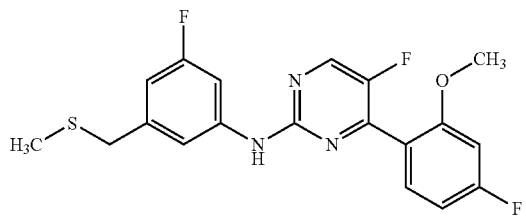 [SMILES: COc1cc(F)ccc1-c1nc(Nc2cc(F)cc(CSC)c2)ncc1F]

A batch with 3-fluoro-5-[(methylsulfanyl)methyl]aniline (1480 mg; 8.64 mmol), 2-chloro-5-fluoro-4-(4-fluoro-2-methoxyphenyl)pyrimidine (2884 mg; 11.2 mmol), chloro(2-dicyclohexylphosphino-2',4',6'-tri-iso-propyl-1,1'-biphenyl)[2-(2-aminoethyl)phenyl]palladium(II) methyl-tertbutylether adduct (536 mg; 0.65 mmol; ABCR GmbH & CO. KG), 2-dicyclohexylphosphino-2',4',6'-triisopropylbiphenyl (309 mg; 0.65 mmol; Aldrich Chemical Company Inc.) and potassium phosphate (9173 mg; 43.2 mmol) in toluene (58.0 ml) and 1-methylpyrrolidin-2-one (11.5 ml) was degassed using argon. The batch was stirred under an atmosphere of argon for 3 hours at 130° C. After cooling, the batch was diluted with saturated aqueous sodium chloride solution and extracted twice with ethyl acetate. The combined organic phases were filtered using a Whatman filter and concentrated. The residue was purified by column chromatography on silica gel (hexane/ethyl acetate 5% to 30%) to give the desired product (2200 mg; 5.62 mmol).

$^1$H NMR (400 MHz, CDCl$_3$, 300K) δ=8.32 (m, 1H), 7.61 (m, 1H), 7.50 (m, 1H), 7.25 (br, 1H), 7.13 (m, 1H), 6.81 (m, 1H), 6.75 (m, 1H), 6.69 (m, 1H), 3.87 (s, 3H), 3.63 (s, 2H), 2.01 (s, 3H).

Preparation of Intermediate 1.5

(rac)-[(3-Fluoro-5-{[5-fluoro-4-(4-fluoro-2-methoxyphenyl)pyrimidin-2-yl]amino}benzyl)(methyl)-λ$^4$-sulfanylidene]ammonium 2,4,6-trimethylbenzenesulfonate (LUEK 4552-3; BAY 1467709)

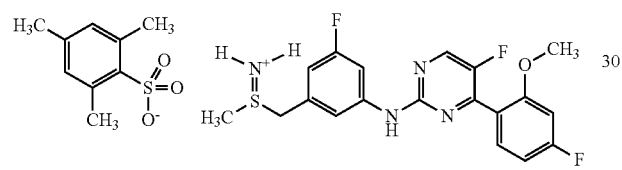

To ethyl o-(mesitylenesulfonyl)acetohydroxamate (1.82 g; 6.39 mmol; Aldrich Chemical Company Inc.) in dioxane (6.5 ml) was added perchloric acid (70%; 6.5 ml) dropwise at 0° C. After additional vigorous stirring for 10 minutes at 0° C., cold water (30 ml) was added and the product MSH was extracted three times with DCM. The combined organic layers were washed with brine and dried (Na$_2$SO$_4$). This solution of MSH in DCM was slowly added to a solution of 5-fluoro-4-(4-fluoro-2-methoxyphenyl)-N-{3-fluoro-5-[(methylsulfanyl)methyl]phenyl}pyrimidin-2-amine (2.50 g; 6.39 mmol) in DCM (6.5 ml) at 0° C. The reaction mixture was stirred at RT for 16 hours. The batch was evaporated until approximately 5 ml of solvent were left. The resulting suspension was suction filtered. The solid was washed with diethylether and dried in vacuo to give the desired product (3.04 g; 5.00 mmol).

$^1$H NMR (400 MHz, DMSO-d6, 300K) δ=10.24 (s, 1H), 8.62 (m, 1H), 7.85 (m, 1H), 7.54 (m, 1H), 7.48 (s, 1H), 7.14 (m, 1H), 6.97 (m, 1H), 6.83 (m, 1H), 6.73 (s, 2H), 5.96 (s, 2H), 4.59 (d, 1H), 4.38 (d, 1H), 3.83 (s, 3H), 3.03 (s, 3H), 2.49 (s, 6H), 2.16 (s, 3H).

Preparation of End Product

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-λ$^4$-sulfanylidene] ammonium 2,4,6-trimethylbenzenesulfonate (300 mg; 0.49 mmol) was dissolved in DMF (1.3 ml) and cooled to 0° C. Sodium carbonate (63 mg; 0.59 mmol) was added followed by N-chlorosuccinimide (79 mg, 0.59 mmol), and the reaction mixture was stirred for 15 min at 0° C. Hexamethyldisilazane (239 mg; 1.48 mmol) was added and the reaction mixture was stirred at room temperature for 18 h. Aqueous sodium chloride solution was added, the product was extracted twice with EtOAc and once with DCM, and the combined organic layers were filtered using a Whatman filter and concentrated. The residue was purified by preparative HPLC to give the desired product (40 mg; 0.09 mmol).

| System: | Agilent: Prep 1200, 2xPrep Pump, DLA, MWD, Prep FC, |
| --- | --- |
| Column: | XBridge C18 5 µm 100 × 30 mm |
| Solvent: | A = H$_2$O + 0.2% Vol. NH$_3$ (32%), B = MeCN |
| Gradient: | 0-10 min 25-55% B, 10-12 min 100% B |
| Flow: | 60 mL/min |
| Temperature: | RT |
| Solution: | 243 mg/3.2 mL DMSO |
| Injection: | 2 × 1.6 mL |
| Detection: | UV 225 nm |

| Retention time in min | Purity in % | Amount in mg |
| --- | --- | --- |
| 5.72-6.42 | 100 | 40 |

$^1$H NMR (400 MHz, DMSO-d6, 300K) δ=10.04 (s, 1H), 8.59 (m, 1H), 7.73 (m, 1H), 7.54 (m, 1H), 7.46 (s, 1H), 7.12 (m, 1H), 6.95 (m, 1H), 6.83 (m, 1H), 4.24 (s, 2H), 3.83 (s, 3H), 2.80 (s, 3H).

Example 2

(rac)-N-{3-[(N,S-Dimethylsulfonodiimidoyl)methyl]-5-fluorophenyl}-5-fluoro-4-(4-fluoro-2-methoxyphenyl)pyrimidin-2-amine (LUEK 4570; BAY 1456927)

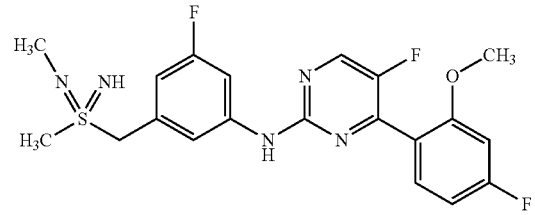 [SMILES: CN=S(C)(=N)Cc1cc(F)cc(Nc2ncc(F)c(-c3ccc(F)cc3OC)n2)c1]

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-λ$^4$-sulfanylidene] ammonium 2,4,6-trimethylbenzenesulfonate (230 mg; 0.38 mmol) was dissolved in DMF (1.0 ml) and cooled to 0° C. Sodium carbonate (48 mg; 0.46 mmol) was added, followed by N-chlorosuccinimide (61 mg, 0.46 mmol), and the reaction mixture was stirred for 15 min at 0° C. A solution of methylamine in ethanol (8M; 0.14 ml; 1.14 mmol) was added and the reaction mixture was stirred at room temperature for 18 h. Aqueous sodium chloride solution was added, the product was extracted twice with EtOAc and the combined organic layers were filtered using a Whatman filter and concentrated. The residue was purified by preparative HPLC to give the desired product (8 mg; 0.02 mmol).

| System: | Waters Autopurificationsystem: Pump 254, Sample Manager 2767, CFO, DAD 2996, ELSD 2424, SQD 3100 |
| --- | --- |
| Column: | XBrigde C18 5 µm 100 × 30 mm |
| Solvent: | A = H$_2$O + 0.2% Vol. NH$_3$ (32%), B = MeCN |

| | | |
|---|---|---|
| Gradient: | 0-8 min 40-60% B | |
| Flow: | 70 mL/min | |
| Temperature: | RT | |
| Solution: | 250 mg/2.5 mL DMSO | |
| Injection: | 1 × 0.5 mL, 2 × 1.0 mL | |
| Detection: | DAD scan range 210-400 nm | |
| | MS ESI+, ESI−, scan range 160-1000 m/z | |
| | ELSD | |

| Retention time in min | Purity in % | Amount in mg |
|---|---|---|
| 2.25-2.50 | 98 | 8 |

$^1$H NMR (400 MHz, DMSO-d6, 300K) δ=10.07 (s, 1H), 8.59 (m, 1H), 7.71 (m, 1H), 7.54 (m, 1H), 7.46 (s, 1H), 7.12 (m, 1H), 6.96 (m, 1H), 6.81 (m, 1H), 4.26 (m, 2H), 3.83 (s, 3H), 2.68 (s, 3H), 2.53 (s, 3H).

Example 3

(rac)-5-Fluoro-4-(4-fluoro-2-methoxyphenyl)-N-{3-fluoro-5-[(S-methyl-N-phenylsulfonodiimidoyl)methyl]phenyl}pyrimidin-2-amine (LUEK 4715; BAY 1746480)

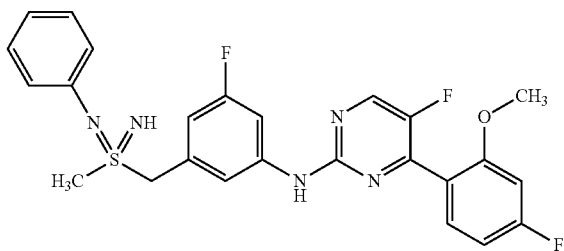 [SMILES: COc1cc(F)ccc1-c1nc(Nc2cc(F)cc(CS(C)(=N)=Nc3ccccc3)c2)ncc1F]

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-λ$^4$-sulfanylidene]ammonium 2,4,6-trimethylbenzenesulfonate (200 mg; 0.33 mmol) was dissolved in DMF (1.0 ml) and cooled to 0° C. Sodium carbonate (42 mg; 0.40 mmol) was added, followed by N-chlorosuccinimide (53 mg, 0.40 mmol), and the reaction mixture was stirred for 15 min at 0° C. Aniline (92 mg; 0.99 mmol) was added and the reaction mixture was stirred at room temperature for 28 h. Water was added, the product was extracted three times with DCM and the combined organic layers were filtered using a Whatman filter and concentrated. The residue was purified by preparative HPLC to give the desired product (29 mg; 0.06 mmol).

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%), B = MeCN |
| Gradient: | 0-0.5 min 25 ml/min auf 70 ml/min 44% B; 0.5-5.5 min 44-64% B |
| Flow: | 70 ml/min |
| Temperature: | RT |
| Solution: | 233 mg/3.9 ml DMSO |
| Injection: | 3 × 1.3 ml |
| Detection: | DAD scan range 210-400 nm MS ESI+, ESI−, scan range 160-1000 m/z ELSD |

| Retention time in min | Purity in % | Amount in mg |
|---|---|---|
| 3.90-4.31 | 99 | 29 |

$^1$H NMR (400 MHz, DMSO-d6, 300K) δ=10.09 (s, 1H), 8.57 (m, 1H), 7.71 (m, 1H), 7.53 (m, 2H), 7.11 (m, 3H), 6.96 (m, 3H), 6.84 (m, 1H), 6.74 (m, 1H), 4.58 (d, 1H), 4.51 (d, 1H), 3.83 (s, 3H), 3.00 (s, 1H), 2.96 (s, 3H).

Example 4

(rac)-5-Fluoro-4-(4-fluoro-2-methoxyphenyl)-N-(3-fluoro-5-{[S-methyl-N-(prop-2-yn-1-yl)sulfonodiimidoyl]methyl}phenyl)pyrimidin-2-amine (LUEK 4717; BAY 1747385)

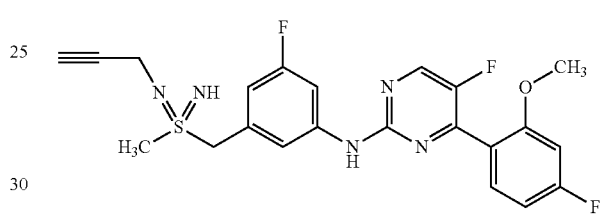

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-λ$^4$-sulfanylidene]ammonium 2,4,6-trimethylbenzenesulfonate (200 mg; 0.33 mmol) was dissolved in DMF (1.0 ml) and cooled to 0° C. Sodium carbonate (42 mg; 0.40 mmol) was added, followed by N-chlorosuccinimide (53 mg, 0.40 mmol), and the reaction mixture was stirred for 15 min at 0° C. Propargylamine (54 mg; 0.99 mmol) was added and the reaction mixture was stirred at room temperature for 24 h. Water was added, the product was extracted three times with DCM and the combined organic layers were washed with aqueous sodium chloride solution, filtered using a Whatman filter and concentrated. The residue was purified by preparative HPLC to give the desired product (19 mg; 0.04 mmol).

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%), B = MeOH |
| Gradient: | 0-0.5 min 25 ml/min auf 70 ml/min 58% B; 0.5-5.5 min 58-66% B |
| Flow: | 70 ml/min |
| Temperature: | RT |
| Solution: | 187 mg/4 ml DMSO/MeOH (3:1) |
| Injection: | 4 × 1 ml |
| Detection: | DAD scan range 210-400 nm MS ESI+, ESI−, scan range 160-1000 m/z ELSD |

| Retention time in min | Purity in % | Amount in mg |
|---|---|---|
| 4.10-4.88 | 96 | 19 |

$^1$H NMR (400 MHz, DMSO-d6, 300K) δ=10.06 (s, 1H), 8.59 (m, 1H), 7.73 (m, 1H), 7.55 (m, 1H), 7.51 (m, 1H), 7.12

(m, 1H), 6.95 (m, 1H), 6.88 (m, 1H), 4.33 (m, 2H), 3.84 (s, 4H), 3.69 (m, 2H), 2.94 (tr, 1H); 2.78 (s, 3H).

Example 5

(rac)-[(3-Fluoro-5-{[5-fluoro-4-(4-fluoro-2-methoxyphenyl)pyrimidin-2-yl]amino}benzyl)(imino)methyl-$\lambda^6$-sulfanylidene]cyanamide (LUEK 4726; BAY 1747857)

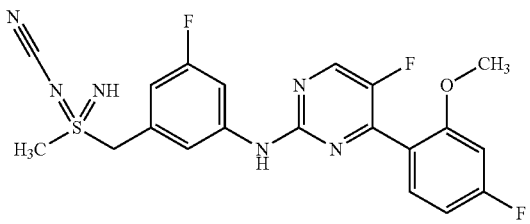 [SMILES: COc1cc(F)ccc1-c1nc(Nc2cc(F)cc(CS(C)(=N)=NC#N)c2)ncc1F]

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-$\lambda^4$-sulfanylidene] ammonium 2,4,6-trimethylbenzenesulfonate (200 mg; 0.33 mmol) was dissolved in DMF (1.0 ml) and cooled to 0° C. Sodium carbonate (42 mg; 0.40 mmol) was added, followed by N-chlorosuccinimide (53 mg, 0.40 mmol), and the reaction mixture was stirred for 15 min at 0° C. Sodium cyanoazanide (63 mg; 0.99 mmol) was added and the reaction mixture was stirred at room temperature for 5 h. Water and aqueous sodium chloride solution were added, the product was extracted three times with DCM and the combined organic layers were washed with aqueous sodium chloride solution, filtered using a Whatman filter and concentrated. The residue was purified by preparative HPLC to give the desired product (36 mg; 0.08 mmol).

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H₂O + 0.1% Vol. HCOOH (99%) |
| | B = MeOH |
| Gradient: | 0-8 min 50-70% B |
| Flow: | 70 ml/min |
| Temperature: | RT |
| Solution: | 186 mg/2.0 ml DMSO |
| Injection: | 1 × 0.5 ml, 2 × 0.75 ml |
| Detection: | DAD scan range 210-400 nm |
| | MS ESI+, ESI−, scan range 160-1000 m/z |
| | ELSD |

| Retention time in min | Purity in % | Amount in mg |
|---|---|---|
| 4.25-4.60 | 97 | 36 | le;2q¹H NMR (400 MHz, DMSO-d6, 300K) δ=10.14 (s, 1H), 8.60 (m, 1H), 7.79 (m, 1H), 7.55 (m, 2H), 7.14 (m, 1H), 6.96 (m, 1H), 6.88 (m, 1H), 4.73 (d, 1H), 4.67 (d, 1H), 4.36 (s, 1H), 3.83 (s, 3H), 3.15 (s, 3H).

Example 6

(rac)-3-{[(3-Fluoro-5-{[5-fluoro-4-(4-fluoro-2-methoxyphenyl)pyrimidin-2-yl]amino}benzyl)(imino)methyl-$\lambda^6$-sulfanylidene]amino}propan-1-ol (LUEK 4681; BAY 1752108)

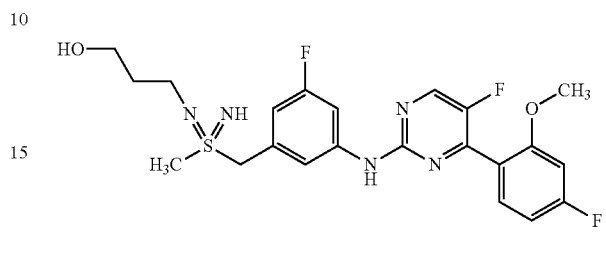

In an oven dry flask, under an atmosphere of argon, (rac)-[(3-fluoro-5-{[5-fluoro-4-(4-fluoro-2-methoxyphenyl)pyrimidin-2-yl]amino}benzyl)(methyl)-$\lambda^4$-sulfanylidene] ammonium 2,4,6-trimethylbenzenesulfonate (200 mg; 0.33 mmol) was dissolved in DMF (1.0 ml) and cooled to 0° C. Sodium carbonate (42 mg; 0.40 mmol) was added, followed by N-chlorosuccinimide (53 mg, 0.40 mmol), and the reaction mixture was stirred for 15 min at 0° C. 3-Aminopropan-1-ol (0.075 ml; 0.99 mmol) was added and the reaction mixture was stirred at room temperature for 27 h. Aqueous sodium chloride solution was added, the product was extracted twice with EtOAc and the combined organic layers were filtered using a Whatman filter and concentrated. The residue was purified by preparative HPLC to give the desired product (10 mg; 0.02 mmol).

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H₂O + 0.2% Vol. NH₃ (32%), |
| | B = MeCN |
| Gradient: | 0-0.5 min 25 mL/min auf 70 mL/min 30% B; 0.5-5.5 min 30-50% B |
| Flow: | 70 mL/min |
| Temperature: | RT |
| Solution: | 22 mg/2 mL DMF/MeOH 1:1 |
| Injection: | 2 × 1 mL |
| Detection: | DAD scan range 210-400 nm |
| | MS ESI+, ESI−, scan range 160-1000 m/z |

| Retention time in min | Purity in % | Amount in mg |
|---|---|---|
| 3.67-4.18 | 99 | 10 |

¹H NMR (400 MHz, DMSO-d6, 300K) δ=10.09 (s, 1H), 8.60 (m, 1H), 7.75 (m, 1H), 7.55 (m, 1H), 7.50 (s, 1H), 7.13 (m, 1H), 6.96 (m, 1H), 6.86 (m, 1H), 4.41 (s, 2H), 3.84 (s, 3H), 3.44 (tr, 2H), 3.00 (m, 2H), 2.83 (s, 3H), 1.55 (m, 2H).

Example 7

4-(2,4-Difluorophenyl)-5-fluoro-N-{3-[(S-methyl-sulfonodiimidoyl)methyl]-5-(pentafluoro-λ⁶-sulfa-nyl)phenyl}pyrimidin-2-amine (LUEK 4751; BAY 1750730)

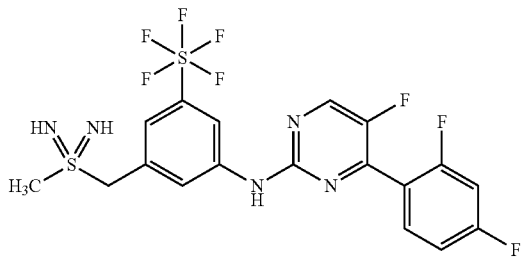 [SMILES: CS(=N)(=N)Cc1cc(Nc2ncc(F)c(-c3ccc(F)cc3F)n2)cc(S(F)(F)(F)(F)F)c1]

Preparation of Intermediate 7.1

2-Chloro-4-(2,4-difluorophenyl)-5-fluoropyrimidine

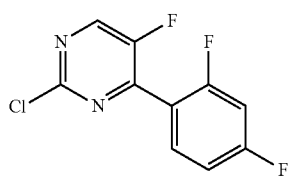 [SMILES: Fc1ccc(-c2nc(Cl)ncc2F)c(F)c1]

Under an atmosphere of argon, a mixture of 2,4-dichloro-5-fluoropyrimidine (19.3 g; 115.5 mmol, Aldrich Chemical Company Inc.), (2,4-difluorophenyl)boronic acid (20.0 g; 127.0 mmol; Aldrich Chemical Company Inc.) and [1,1'-bis(diphenylphosphino)ferrocene]dichloropalladium(II) (9.4 g; 11.5 mmol; Aldrich Chemical Company Inc.) in a 2M solution of potassium carbonate (173 mL) and 1,2-dimethoxyethane (496 mL) was stirred for 90 minutes at 90° C. After cooling, the batch was diluted with ethyl acetate and washed with diluted aqueous sodium chloride solution. The organic phase was filtered using a Whatman filter and concentrated. The residue was first purified by chromatography (hexane/ethyl acetate 20% to 50%) and then digested with hexane to give the desired product (15.0 g; 61.2 mmol).

¹H NMR (400 MHz, CDCl₃, 300K) δ=8.56 (m, 1H), 7.73 (m, 1H), 7.07 (m, 1H), 6.95 (m, 1H).

Preparation of Intermediate 7.2

[3-{[4-(2,4-Difluorophenyl)-5-fluoropyrimidin-2-yl]amino}-5-(pentafluoro-λ⁶-sulfanyl)phenyl]methanol (LUEK 4714)

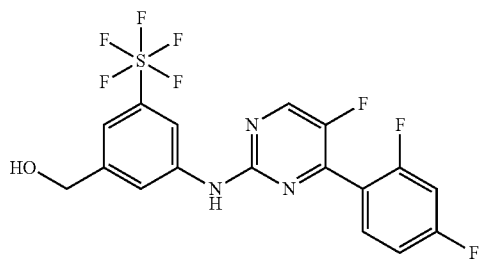 [SMILES: OCc1cc(Nc2ncc(F)c(-c3ccc(F)cc3F)n2)cc(S(F)(F)(F)(F)F)c1]

To a mixture of 2-chloro-4-(2,4-difluorophenyl)-5-fluoropyrimidin (2.50 g; 10.22 mmol) and [3-amino-5-(pentafluoro-λ⁶-sulfanyl)phenyl]methanol ([CAS-Nr. 1427316-37-7] 2.57 g; 10.3 mmol) in 1-butanol (5 mL), trifluoroacetic acid (0.75 mL; 9.74 mmol) was added and the mixture was stirred for 20 hours at 140° C. in a sealed tube. While cooling to room temperature the desired product precipitated and was separated by filtration. While concentrating the mother liquor, more product precipitated and was separated by filtration. The solid product fractions were combined and dried in vacuo to give the desired product (2.59 g; 5.66 mmol).

¹H NMR (400 MHz, DMSO-d6) δ [ppm]=10.30 (s, 1 H), 8.76 (d, 1 H), 8.41 (s, 1 H), 7.83-7.89 (m, 1 H), 7.75-7.83 (m, 1 H), 7.45-7.56 (m, 1 H), 7.38 (s, 1 H), 7.26-7.35 (m, 1 H), 5.46 (br. s., 1 H), 4.54 (d, 2 H).

Preparation of Intermediate 7.3

N-[3-(Chloromethyl)-5-(pentafluoro-λ⁶-sulfanyl)phenyl]-4-(2,4-difluorophenyl)-5-fluoropyrimidin-2-amine (LUEK 4719)

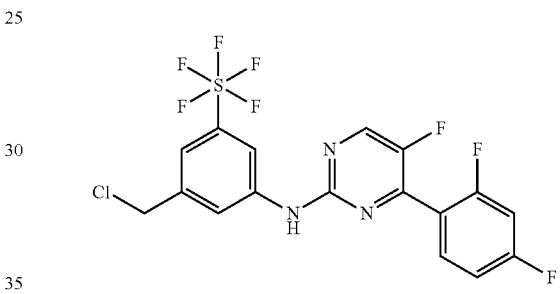

A suspension of [3-{[4-(2,4-difluorophenyl)-5-fluoropyrimidin-2-yl]amino}-5-(pentafluoro-λ⁶-sulfanyl)phenyl]methanol (2.59 g; 5.38 mmol) in DCM (15 mL) at 0° C. was treated with thionyl chloride (3.1 mL, 43.03 mmol). The mixture was stirred for 3 hours at 0 to 25° C. The batch was concentrated to give the crude product (2.77 g) which was used without further purification.

Preparation of Intermediate 7.4

4-(2,4-Difluorophenyl)-5-fluoro-N-{3-[(methylsulfanyl)methyl]-5-(pentafluoro-λ⁶-sulfanyl)phenyl}pyrimidin-2-amine (BAY 1247168, LUEK 4722)

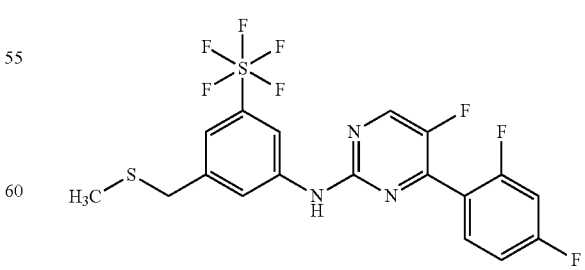

Sodium methanethiolate (0.57 g; 8.12 mmol) was added in portions to a stirred solution of crude N-[3-(chloromethyl)-5-(pentafluoro-λ⁶-sulfanyl)phenyl]-4-(2,4-difluorophenyl)-5-fluoropyrimidin-2-amine (2.77 g; 5.41 mmol) in ethanol (15 mL) at −40° C. The cold bath was removed and the batch was stirred at room temperature for 3 hours. The batch was cooled to −40° C. again and additional sodium methanethiolate (0.19 g; 2.71 mmol) was added in portions. The cold bath was removed and the batch was stirred at room temperature for 1 hour. The batch was diluted with saturated aqueous sodium chloride solution and extracted twice with ethyl acetate. The combined organic layers were filtered using a Whatman filter and concentrated to give the crude product that was recrystallized from ethyl acetate/hexane to give the desired product (2.12 g; 4.31 mmol).

$^1$H NMR (400 MHz, DMSO-d6, 300K) δ [ppm]=8.45 (s, 1H), 8.29 (s, H), 7.65 (m, 1H), 7.64 (s, 1H), 7.37 (m, 2H), 7.09 (m, 1H), 7.01 (m, 1H), 3.73 (s, 2H), 2.05 (s, 3H).

Preparation of Intermediate 7.5

(rac)-{[3-{[4-(2,4-Difluorophenyl)-5-fluoropyrimidin-2-yl]amino}-5-(pentafluoro-$\lambda^6$-sulfanyl)benzyl](methyl)-$\lambda^4$-sulfanylidene}ammonium 2,4,6-trimethylbenzenesulfonate (LUEK 4734; BAY 1733070)

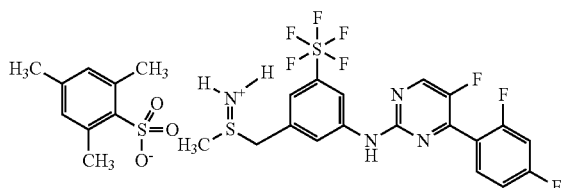

To ethyl o-(mesitylenesulfonyl)acetohydroxamate (175 mg; 0.62 mmol; Aldrich Chemical Company Inc.) in dioxane (6.0 ml) was added perchloric acid (70%; 6.1 ml) dropwise at 0° C. After additional vigorous stirring for 10 minutes at 0° C., cold water (30 ml) was added and the product MSH was extracted twice with DCM. The combined organic layers were washed with brine and filtered using a Whatman filter. This solution of MSH in DCM was slowly added to a solution of 4-(2,4-difluorophenyl)-5-fluoro-N-{3-[(methylsulfanyl)methyl]-5-(pentafluoro-$\lambda^6$-sulfanyl)phenyl}pyrimidin-2-amine (300 mg; 0.62 mmol) in DCM (6.0 ml) at 0° C. The reaction mixture was stirred at RT for 16 hours. The batch was evaporated until approximately 2 ml of solvent were left and diethylether and hexane were added. The resulting suspension was kept at 5° C. overnight and then suction filtered. The solid was washed with diethylether and dried in vacuo to give the desired product (270 mg; 0.38 mmol).

$^1$H NMR (400 MHz, DMSO-d6, 300K) δ=10.49 (s, 1H), 8.77 (m, 1H), 8.57 (m, 1H), 7.91 (s, 1H), 7.81 (m, 1H), 7.58 (m, 1H), 7.50 (s, 1H), 7.33 (m, 1H), 6.72 (s, 2H), 6.00 (br, 2H), 4.69 (d, 1H), 4.48 (d, 1H), 3.06 (s, 3H), 2.49 (s, 6H), 2.15 (s, 3H).

Preparation of End Product

In an oven dry flask, under an atmosphere of argon (rac)-{[3-{[4-(2,4-Difluorophenyl)-5-fluoropyrimidin-2-yl]amino}-5-(pentafluoro-$\lambda^6$-sulfanyl)benzyl](methyl)-$\lambda^4$-sulfanylidene}ammonium 2,4,6-trimethylbenzenesulfonate (250 mg; 0.36 mmol) was dissolved in DMF (1.1 ml) and cooled to 0° C. Sodium carbonate (45 mg; 0.43 mmol) was added, followed by N-chlorosuccinimide (57 mg; 0.43 mmol), and the reaction mixture was stirred for 15 min at 0° C. Hexamethyldisilazane (172 mg; 1.07 mmol) was added and the reaction mixture was stirred at room temperature for 19 h. Aqueous sodium chloride solution was added, the product was extracted twice with EtOAc and once with DCM and the combined organic layers were filtered using a Whatman filter and concentrated. The residue was purified by preparative HPLC to give the desired product (41 mg; 0.08 mmol).

| System: | Waters Autopurificationsystem: Pump 254, Sample Manager 2767, CFO, DAD 2996, ELSD 2424, SQD 3100 |
|---|---|
| Column: | YMC-Triart 5 μm 100 × 30 mm |
| Solvent: | A = H$_2$O + 0.2% Vol. NH$_3$ (32%), B = MeCN |
| Gradient: | 0.5 min inlet (24% B, 25 mL/min); 0.5-5.5 min 48-68% B |
| Flow: | 70 mL/min |
| Temperature: | RT |
| Solution: | 206 mg/2.0 mL DMSO/MeOH |
| Injection: | 4 × 0.5 mL |
| Detection: | DAD scan range 210-400 nm MS ESI+, ESI−, scan range 160-1000 m/z |

| Retention time in min | Purity in % | Amount in mg |
|---|---|---|
| 3.1-3.4 | 100 | 41 |

$^1$H NMR (400 MHz, DMSO-d6, 300K) δ=10.32 (s, 1H), 8.75 (m, 1H), 8.46 (m, 1H), 7.94 (s, 1H), 7.84 (m, 1H), 7.55 (m, 1H), 7.49 (m, 1H), 7.32 (m, 1H), 4.37 (s, 2H), 2.83 (s, 3H), 2.80 (s, 3H), 2.41 (s, 1H).

Example 8

5-Fluoro-4-(4-fluoro-2-methoxyphenyl)-N-{3-[(S-methylsulfonodiimidoyl)methyl]-5-(pentafluoro-$\lambda^6$-sulfanyl)phenyl}pyrimidin-2-amine (LUEK 4792; BAY 1809271)

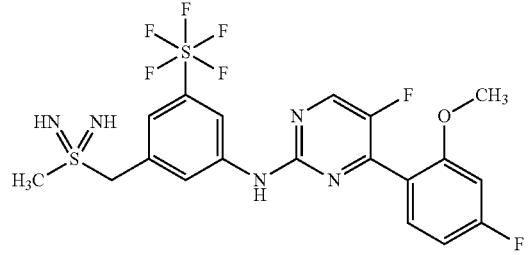 [SMILES: COc1cc(F)ccc1-c1nc(Nc2cc(CS(C)(=N)=N)cc(S(F)(F)(F)(F)F)c2)ncc1F]

Preparation of Intermediate 8.1

[3-{[5-fluoro-4-(4-fluoro-2-methoxyphenyl)pyrimidin-2-yl]amino}-5-(pentafluoro-$\lambda^6$-sulfanyl)phenyl]methanol (BAY 1201874, LUEK 3963-4)

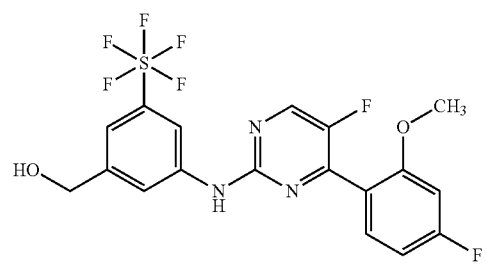 [SMILES: COc1cc(F)ccc1-c1nc(Nc2cc(CO)cc(S(F)(F)(F)(F)F)c2)ncc1F]

To a mixture of 2-chloro-5-fluoro-4-(4-fluoro-2-methoxyphenyl)pyrimidine (2.00 g; 7.79 mmol; see Intermediate 1.3) and [3-amino-5-(pentafluoro-$\lambda^6$-sulfanyl)phenyl]methanol ([CAS-Nr. 1427316-37-7] 1.96 g; 7.87 mmol) in 1-butanol (3.80 mL), trifluoroacetic acid (0.57 mL; 7.40 mmol) was added and the mixture was stirred for 16 hours at 140° C. in a sealed tube. The batch was cooled and concentrated and digested with DCM to give the crude product (2.28 g) which used without further purification.

$^1$H NMR (400 MHz, DMSO-d6) δ [ppm]=10.20 (s, 1H), 8.63 (m, 1H), 8.39 (s, 1H), 7.85 (m, 1H), 7.54 (m, 1H), 7.36 (s, 1H), 7.13 (m, 1H), 6.95 (m, 1H), 4.53 (br, 2H), 3.83 (s, 3H).

Preparation of Intermediate 8.2

N-[3-(chloromethyl)-5-(pentafluoro-$\lambda^6$-sulfanyl)phenyl]-5-fluoro-4-(4-fluoro-2-methoxyphenyl)pyrimidin-2-amine (LUEK 3990-4)

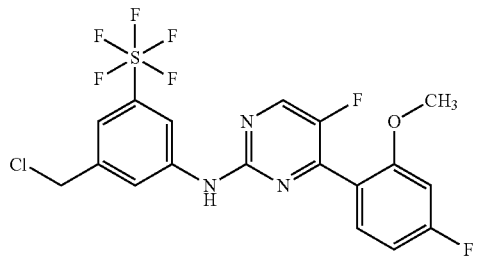 [SMILES: COc1cc(F)ccc1-c1nc(Nc2cc(CCl)cc(S(F)(F)(F)(F)F)c2)ncc1F]

A suspension of crude [3-{[5-fluoro-4-(4-fluoro-2-methoxyphenyl)pyrimidin-2-yl]amino}-5-(pentafluoro-$\lambda^6$-sulfanyl)phenyl]methanol (2.26 g) in DCM (12.0 mL) at 0° C. was treated with thionyl chloride (2.8 mL, 38.6 mmol). The mixture was stirred for 3 hours at 0 to 25° C. The batch was concentrated to give the crude product (2.30 g) which was used without further purification.

Preparation of Intermediate 8.3

5-fluoro-4-(4-fluoro-2-methoxyphenyl)-N-{3-[(methylsulfanyl)methyl]-5-(pentafluoro-$\lambda^6$-sulfanyl)phenyl}pyrimidin-2-amine (LUEK 3993-6; BAY 1204339)

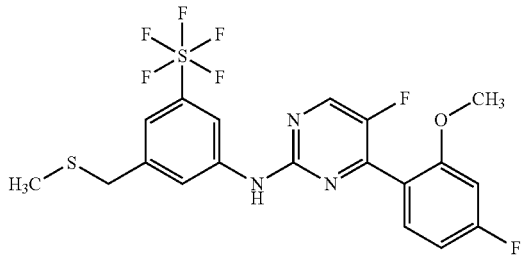 [SMILES: COc1cc(F)ccc1-c1nc(Nc2cc(CSC)cc(S(F)(F)(F)(F)F)c2)ncc1F]

Sodium methanethiolate (0.50 g; 7.07 mmol) was added in portions to a stirred solution of crude N-[3-(chloromethyl)-5-(pentafluoro-$\lambda^6$-sulfanyl)phenyl]-5-fluoro-4-(4-fluoro-2-methoxyphenyl)pyrimidin-2-amine (2.30 g) in ethanol (15 mL) at −40° C. The cold bath was removed and the batch was stirred at room temperature for 5 hours. The batch was cooled to −40° C. again and additional sodium methanethiolate (0.17 g; 2.36 mmol) was added in portions. The cold bath was removed and the batch was stirred at room temperature for 30 hours. The batch was cooled to −40° C. again and additional sodium methanethiolate (0.33 g; 4.71 mmol) was added in portions. The cold bath was removed and the batch was stirred at room temperature for 16 hours. The batch was diluted with saturated aqueous sodium chloride solution and extracted twice with ethyl acetate. The combined organic layers were filtered using a Whatman filter and concentrated. The residue was purified by column chromatography on silica gel (DCM/EtOH 98:2) to give the desired product (1.20 g; 2.40 mmol).

$^1$H NMR (400 MHz, CDCl$_3$, 300K) δ [ppm]=8.33 (m, 1H), 8.23 (m, 1H), 7.61 (br, 1H), 7.51 (m, 1H), 7.33 (m, 2H), 6.81 (m, 1H), 6.75 (m, 1H), 3.86 (s, 3H), 3.69 (s, 2H), 2.02 (s, 3H).

Preparation of Intermediate 8.4

(rac)-{[3-{[5-fluoro-4-(4-fluoro-2-methoxyphenyl)pyrimidin-2-yl]amino}-5-(pentafluoro-$\lambda^6$-sulfanyl)benzyl](methyl)-$\lambda^4$-sulfanylidene}ammonium 2,4,6-trimethylbenzenesulfonate (LUEK 4789-1)

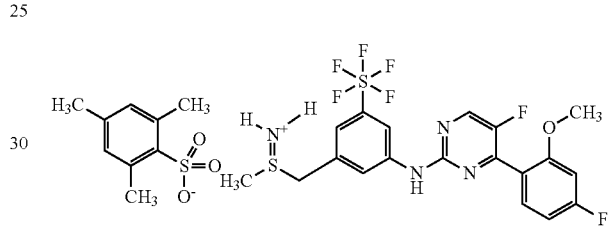

To ethyl o-(mesitylenesulfonyl)acetohydroxamate (365 mg; 1.28 mmol; Aldrich Chemical Company Inc.) in dioxane (12.7 ml) was added perchloric acid (70%; 12.7 ml) dropwise at 0° C. After additional vigorous stirring for 10 minutes at 0° C., cold water (60 ml) was added and the product MSH was extracted twice with DCM. The combined organic layers were washed with brine and filtered using a Whatman filter. This solution of MSH in DCM was slowly added to a solution of 5-fluoro-4-(4-fluoro-2-methoxyphenyl)-N-{3-[(methylsulfanyl)methyl]-5-(pentafluoro-$\lambda^6$-sulfanyl)phenyl}pyrimidin-2-amine (638 mg; 1.28 mmol) in DCM (12.7 ml) at 0° C. The reaction mixture was stirred at RT for 40 hours. UPLC-MS analysis revealed that approximately half of the 5-fluoro-4-(4-fluoro-2-methoxyphenyl)-N-{3-[(methylsulfanyl)methyl]-5-(pentafluoro-$\lambda^6$-sulfanyl)phenyl}pyrimidin-2-amine had not reacted and therefore the same amount of MSH in DCM was added to the reaction mixture at 0° C. The reaction mixture was stirred at RT for 8 hours. The batch was evaporated until approximately 5 ml of solvent were left and diethylether and hexane were added. The resulting suspension was kept at 5° C. for 5 days and then suction filtered. The solid was washed with diethylether and dried in vacuo to give the desired product (734 mg; 1.03 mmol).

$^1$H NMR (400 MHz, DMSO-d6, 300K) δ=10.40 (s, 1H), 8.64 (m, 1H), 8.56 (m, 1H), 7.91 (s, 1H), 7.55 (m, 2H), 7.15 (m, 1H), 6.96 (m, 1H), 6.73 (s, 2H), 5.98 (s, 2H), 4.68 (d, 1H), 4.47 (d, 1H), 3.83 (s, 3H), 3.05 (s, 3H), 2.49 (s, 6H), 2.15 (s, 3H).

Preparation of End Product

In an oven dry flask, under an atmosphere of argon (rac)-{[3-{[5-fluoro-4-(4-fluoro-2-methoxyphenyl)pyrimidin-2-yl]amino}-5-(pentafluoro-λ⁶-sulfanyl)benzyl](methyl)-λ⁴-sulfanylidene}ammonium 2,4,6-trimethylbenzenesulfonate (250 mg; 0.35 mmol) was dissolved in DMF (1.3 ml) and cooled to 0° C. Sodium carbonate (45 mg; 0.42 mmol) was added, followed by N-chlorosuccinimide (56 mg, 0.42 mmol), and the reaction mixture was stirred for 15 min at 0° C. Hexamethyldisilazane (169 mg; 1.05 mmol) was added and the reaction mixture was stirred at room temperature for 4 h. Aqueous sodium chloride solution was added, the product was extracted twice with EtOAc and once with DCM and the combined organic layers were filtered using a Whatman filter and concentrated. The residue was purified by preparative HPLC to give the desired product (12 mg; 0.02 mmol).

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.2% Vol. NH₃ (32%), |
| | B = MeCN |
| Gradient: | 0-0.5 min 25 mL/min to 70 mL/min 38% B; 0.5-5.5 min 38-58% B |
| Flow: | 70 mL/min |
| Temperature: | RT |
| Solution: | 73 mg/2.0 mL DMSO |
| Injection: | 2 × 1.0 mL |
| Detection: | DAD scan range 210-400 nm |
| | MS ESI+, ESI−, scan range 160-1000 m/z |

| Retention time in min | Purity in % | Amount in mg |
|---|---|---|
| 3.88-4.14 | 99 | 12 |

¹H NMR (400 MHz, DMSO-d6, 300K) δ=10.22 (s, 1H), 8.62 (m, 1H), 8.45 (m, 1H), 7.92 (s, 1H), 7.54 (m, 2H), 7.12 (m, 1H), 6.95 (m, 1H), 4.36 (s, 2H), 3.84 (s, 3H), 2.82 (s, 3H).

The following Table 1 provides an overview on the compounds described in the example section:

TABLE 1

| Example No. | Structure | Name of compound |
|---|---|---|
| 1 | 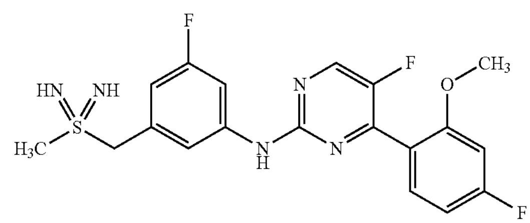 [SMILES: COc1cc(F)ccc1-c1nc(Nc2cc(F)cc(CS(C)(=N)=N)c2)ncc1F] | 5-Fluoro-4-(4-fluoro-2-methoxyphenyl)-N-{3-fluoro-5-[(S-methylsulfonodiimidoyl)methyl]phenyl}pyrimidin-2-amine |
| 2 | 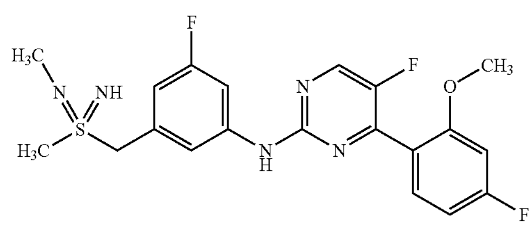 [SMILES: CN=S(C)(=N)Cc1cc(F)cc(Nc2ncc(F)c(-c3ccc(F)cc3OC)n2)c1] | (rac)-N-{3-[(N,S-Dimethylsulfonodiimidoyl)methyl]-5-fluorophenyl}-5-fluoro-4-(4-fluoro-2-methoxyphenyl)pyrimidin-2-amine |
| 3 | 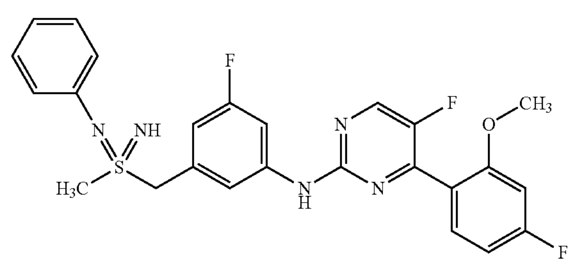 [SMILES: COc1cc(F)ccc1-c1nc(Nc2cc(F)cc(CS(C)(=N)=Nc3ccccc3)c2)ncc1F] | (rac)-5-fluoro-4-(4-fluoro-2-methoxyphenyl)-N-{3-fluoro-5-[(S-methyl-N-phenylsulfonodiimidoyl)methyl]phenyl}pyrimidin-2-amine |
| 4 | 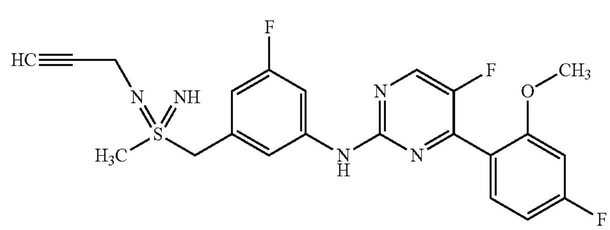 [SMILES: C#CCN=S(C)(=N)Cc1cc(F)cc(Nc2ncc(F)c(-c3ccc(F)cc3OC)n2)c1] | (rac)-5-Fluoro-4-(4-fluoro-2-methoxyphenyl)-N-(3-fluoro-5-{[S-methyl-N-(prop-2-yn-1-yl)sulfonodiimidoyl]methyl}phenyl)pyrimidin-2-amine |

TABLE 1-continued

| Example No. | Structure | Name of compound |
|---|---|---|
| 5 | 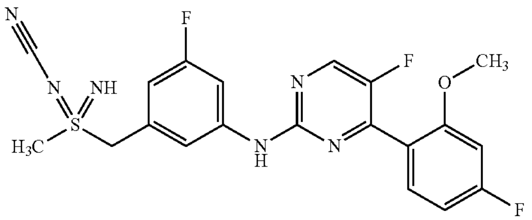 [SMILES: COc1cc(F)ccc1-c1nc(Nc2cc(F)cc(CS(C)(=N)=NC#N)c2)ncc1F] | (rac)-[(3-Fluoro-5-{[5-fluoro-4-(4-fluoro-2-methoxyphenyl)pyrimidin-2-yl]amino}benzyl)(imino)methyl-$\lambda^6$-sulfanylidene]cyanamide |
| 6 | 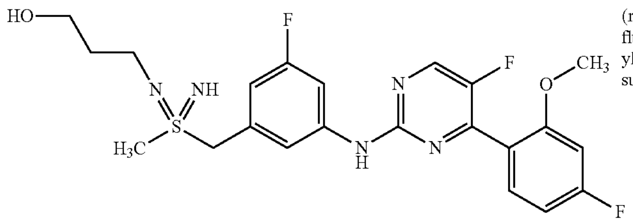 | (rac)-3-{[(3-Fluoro-5-{[5-fluoro-4-(4-fluoro-2-methoxyphenyl)pyrimidin-2-yl]amino}benzyl)(imino)methyl-$\lambda^6$-sulfanylidene]amino}propan-1-ol |
| 7 | 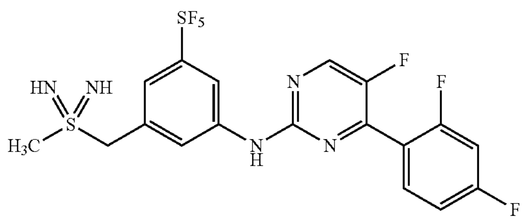 | 4-(2,4-Difluorophenyl)-5-fluoro-N-{3-[(S-methylsulfonodiimidoyl)methyl]-5-(pentafluoro-$\lambda^6$-sulfanyl)phenyl}pyrimidin-2-amine |
| 8 | 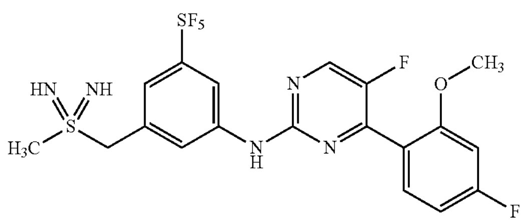 | 5-Fluoro-4-(4-fluoro-2-methoxyphenyl)-N-{3-[(S-methylsulfonodiimidoyl)methyl]-5-(pentafluoro-$\lambda^6$-sulfanyl)phenyl}pyrimidin-2-amine |

Results:
Table 2: Inhibition for CDK9 and CDK2 of compounds according to the present invention The IC$_{50}$ (inhibitory concentration at 50% of maximal effect) values are indicated in nM, "n.t." means that the compounds have not been tested in the respective assay.

①: Example Number
②: CDK9: CDK9/CycT1 kinase assay as described under Method 1a. of Materials and Methods
③: CDK2: CDK2/CycE kinase assay as described under Method 2. of Materials and Methods
④: Selectivity CDK9 over CDK2: IC$_{50}$ (CDK2)/IC$_{50}$ (CDK9) according to Methods 1a. and 2a. of Materials and Methods
⑤: high ATP CDK9: CDK9/CycT1 kinase assay as described under Method 1b. of Materials and Methods
⑥: high ATP CDK2: CDK2/CycE kinase assay as described under Method 2b. of Materials and Methods
⑦: Selectivity high ATP CDK9 over high ATP CDK2: IC$_{50}$ (high ATP CDK2)/IC$_{50}$ (high ATP CDK9) according to Methods 1b. and 2b. of Materials and Methods

TABLE 2

| ① | Structure | ② | ③ | ④ | ⑤ | ⑥ | ⑦ |
|---|---|---|---|---|---|---|---|
| 1 | 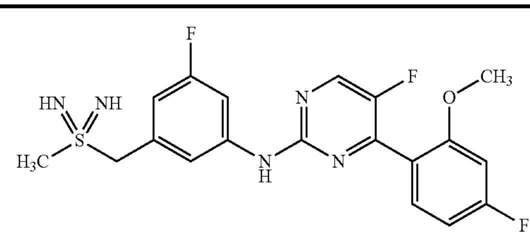 | 13 | 790 | 62 | 104 | 10500 | 101 |

TABLE 2-continued

| ① | Structure | ② | ③ | ④ | ⑤ | ⑥ | ⑦ |
| --- | --- | --- | --- | --- | --- | --- | --- |
| 2 | (structure) | 51 | 1300 | 87 | 389 | 13000 | 33 |
| 3 | (structure) | n.t. | 1400 | n.t. | n.t. | n.t. | n.t. |
| 4 | (structure) | 12 | 580 | 48 | 22 | 4290 | 195 |
| 5 | (structure) | 4 | 190 | 48 | 3 | 1470 | 490 |
| 6 | (structure) | 10 | 970 | 97 | 93 | 19800 | 213 |
| 7 | (structure) | 17 | 2300 | 135 | 26 | 20000 | 769 |

TABLE 2-continued

| ① | Structure | ② | ③ | ④ | ⑤ | ⑥ | ⑦ |
|---|---|---|---|---|---|---|---|
| 8 | 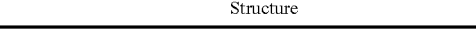 | 4 | 400 | 100 | 3 | 2990 | 997 |

Tables 3a and 3b: Inhibition of proliferation of HeLa, HeLa-MaTu-ADR, NCI-H460, DU145, Caco-2, B16F10, A2780 and MOLM-13 cells by compounds according to the present invention, determined as described under Method 3. of Materials and Methods. All $IC_{50}$ (inhibitory concentration at 50% of maximal effect) values are indicated in nM, "n.t." means that the compounds have not been tested in the respective assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation
⑨: Inhibition of MOLM-13 cell proliferation

TABLE 3a

Indications represented by cell lines

| Cell line | Source | Indication |
|---|---|---|
| HeLa | ATCC | Human cervical tumour |
| HeLa-MaTu-ADR | EPO-GmbH Berlin | Multidrug-resistant human cervical carcinoma |
| NCI-H460 | ATCC | Human non-small cell lung carcinoma |
| DU 145 | ATCC | Hormone-independent human prostate carcinoma |
| Caco-2 | ATCC | Human colorectal carcinoma |
| B16F10 | ATCC | Mouse melanoma |
| A2780 | ECACC | Human ovarian carcinoma |
| MOLM-13 | DSMZ | Human acute myeloid leukemia |

TABLE 3b

Inhibition of proliferation

| ① | Structure | ② | ③ | ④ | ⑤ | ⑥ | ⑦ | ⑧ | ⑨ |
|---|---|---|---|---|---|---|---|---|---|
| 1 | 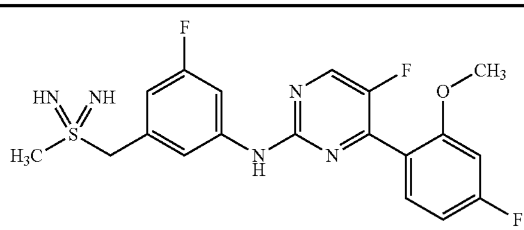 | 252 | 327 | 351 | 341 | 386 | 532 | 201 | n.t. |
| 2 | 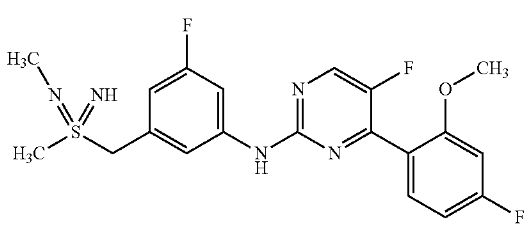 [SMILES: CN=S(C)(=N)Cc1cc(F)cc(Nc2ncc(F)c(-c3ccc(F)cc3OC)n2)c1] | 412 | 793 | 968 | 636 | 849 | 1120 | 333 | n.t. |
| 3 | 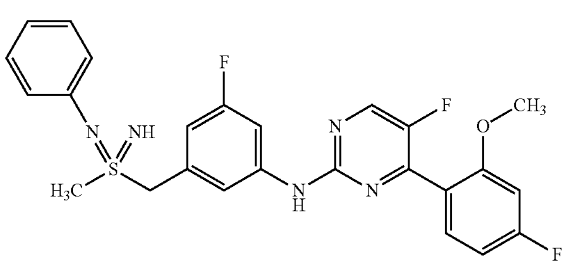 [SMILES: COc1cc(F)ccc1-c1nc(Nc2cc(F)cc(CS(C)(=N)=Nc3ccccc3)c2)ncc1F] | 991 | 863 | 1090 | 1050 | 1000 | 1270 | 548 | n.t. |

TABLE 3b-continued

Inhibition of proliferation

| ① | Structure | ② | ③ | ④ | ⑤ | ⑥ | ⑦ | ⑧ | ⑨ |
|---|---|---|---|---|---|---|---|---|---|
| 4 | (structure) | 535 | 696 | 935 | 581 | 847 | 1130 | 355 | n.t. |
| 5 | (structure) | 73 | 80 | 193 | 42 | 94 | 122 | 35 | n.t. |
| 6 | (structure) | 507 | n.t. | n.t. | n.t. | n.t. | n.t. | n.t. | n.t. |
| 7 | (structure) | 346 | n.t. | n.t. | n.t. | n.t. | n.t. | 337 | 244 |
| 8 | (structure) | 104 | 194 | 149 | 130 | 144 | 237 | n.t. | 36 |

Table 4: Thermodynamic solubility of compounds according to the present invention in water at pH 6.5 as determined by the equilibrium shake flask methods described under Method 4a. and 4b. of Materials and Methods; "n.t." means that the compounds have not been tested in the respective assay.

①: Example Number
②: Aqueous Solubility pH 6.5 [mg/L], thermodynamic from DMSO solution as described under Method 4a. of Materials and Methods
③: Aqueous Solubility pH 6.5 [mg/L], thermodynamic from powder as described under Method 4b. of Materials and Methods

| ① | Structure of compound | ② | ③ |
|---|---|---|---|
| 1 | | 155 | 91 |
| 2 | | 97 | n.t. |
| 3 | | 1.4 | n.t. |
| 6 | | 259 | n.t. |
| 7 | | 1.2 | n.t. |
| 8 | | 2.2 | n.t. |

Table 5: Caco-2 permeation of compounds according to the present invention, determined as described under Method 5. of Materials and Methods.

①: Example Number
②: Concentration of test compound indicated in μM.
③: $P_{app}$ A–B ($M_{art}$) indicated in [nm/s]
④: $P_{app}$ B–A ($M_{art}$) indicated in [nm/s]
⑤: Efflux ratio

TABLE 5

| ① | Structure of compound | ② | ③ | ④ | ⑤ |
|---|---|---|---|---|---|
| 1 | | 2 | 50.0 | 280.0 | 5.6 |
| 5 | | 2 | 28.8 | 198.7 | 6.9 |
| 7 | | 2 | 32.1 | 35.7 | 1.1 |
| 8 | | 2 | 33.3 | 51.9 | 1.6 |

The invention claimed is:
1. A compound of formula (I)

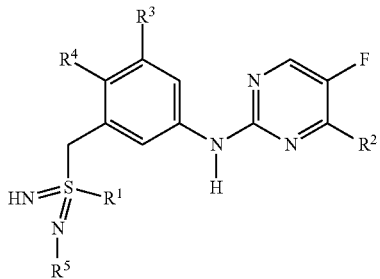

wherein:
R¹ is a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —NH₂, alkylamino-, dialkylamino-, acetylamino-, N-methyl-N-acetylamino-, cyclic amines, —OP(=O)(OH)₂, —C(=O)OH, and —C(=O)NH₂;
R² is a group selected from

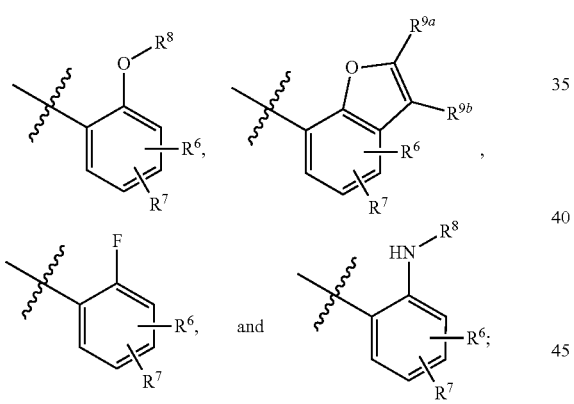

R³ is a group selected from a fluoro atom, chloro atom, bromo atom, cyano, —SF₅, $C_1$-$C_3$-alkyl-, $C_1$-$C_3$-alkoxy-, halo-$C_1$-$C_3$-alkyl-, and $C_1$-$C_3$-fluoroalkoxy-;
R⁴ is a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-;
R⁵ is a group selected from a hydrogen atom, cyano, —S(=O)₂R¹⁰, $C_1$-$C_6$-alkyl-, $C_3$-$C_6$-alkenyl-, $C_3$-$C_6$-alkynyl-, $C_3$-$C_7$-cycloalkyl-, heterocyclyl-, phenyl, and heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, —NH₂, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

R⁶ and R⁷ are, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-;
R⁸ is a group selected from
a) a $C_1$-$C_6$-alkyl group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl,
wherein said $C_3$-$C_7$-cycloalkyl-, heterocyclyl-, phenyl or heteroaryl group is optionally substituted with one, two or three substituents, identically or differently, selected from the group consisting of halogen, hydroxy, $C_1$-$C_3$-alkyl-, $C_1$-$C_3$-alkoxy-, —NH₂, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;
b) a phenyl-$C_1$-$C_3$-alkyl- group, the phenyl group of which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;
c) a heteroaryl-$C_1$-$C_3$-alkyl- group, the heteroaryl group of which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;
d) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-; and
e) a heterocyclyl-$C_1$-$C_3$-alkyl- group, the heterocyclyl group of which is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-;
R⁹ᵃ and R⁹ᵇ are, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-; and
R¹⁰ is a group selected from $C_1$-$C_6$-alkyl-, halo-$C_1$-$C_3$-alkyl-, $C_3$-$C_7$-cycloalkyl-, heterocyclyl-, phenyl, benzyl and heteroaryl,
wherein said group is optionally substituted with one, two or three substituents, identically or differently, selected from the group consisting of halogen, hydroxy, $C_1$-$C_3$-alkyl-, $C_1$-$C_3$-alkoxy-, —NH₂, alkylamino-, dialkylamino-, acetylamino-, N-methyl-N-acetylamino-, cyclic amines, halo-$C_1$-$C_3$-alkyl-, and $C_1$-$C_3$-fluoroalkoxy-, or an enantiomer, diastereomer, salt, solvate or salt of solvate thereof.

2. The compound of formula (I) according to claim 1, or an enantiomer, diastereomer, salt, solvate or salt of solvate thereof, wherein:

$R^1$ is a $C_1$-$C_6$-alkyl or $C_3$-$C_5$-cycloalkyl group,
wherein said group is optionally substituted with one substituent selected from the group consisting of hydroxy, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(=O)(OH)$_2$, —C(=O)OH, and —C(=O)$NH_2$;

$R^2$ is a group selected from

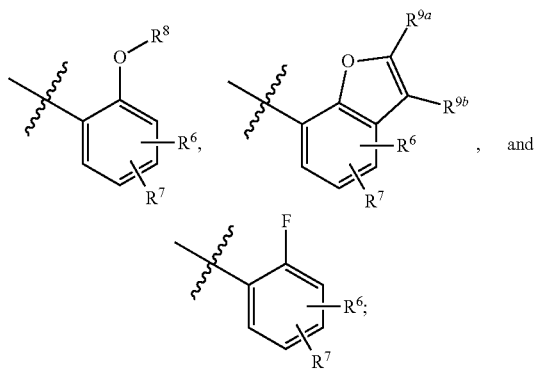

$R^3$ is a group selected from a fluoro atom, chloro atom, —$SF_5$, $C_1$-$C_3$-alkyl and fluoro-$C_1$-$C_3$-alkyl-;

$R^4$ is a hydrogen atom or fluoro atom;

$R^5$ represents a group selected from a hydrogen atom, cyano, —S(=O)$_2$$R^{10}$, $C_1$-$C_6$-alkyl-, $C_3$-$C_6$-alkenyl-, $C_3$-$C_6$-alkynyl-, $C_3$-$C_5$-cycloalkyl-, and phenyl,
wherein said $C_1$-$C_6$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, and $C_1$-$C_2$-fluoroalkoxy-;

$R^6$ and $R^7$ are, independently from each other, a group selected from a hydrogen atom, fluoro atom, chloro atom, bromo atom, cyano, $C_1$-$C_2$-alkyl-, $C_1$-$C_2$-alkoxy-, fluoro-$C_1$-$C_2$-alkyl-, and $C_1$-$C_2$-fluoroalkoxy-;

$R^8$ is a group selected from a) a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, $C_3$-$C_5$-cycloalkyl-, and phenyl,
wherein said $C_3$-$C_5$-cycloalkyl- or phenyl group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, and $C_1$-$C_2$-fluoroalkoxy-;

b) a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, and $C_1$-$C_3$-alkoxy-;

c) a heteroaryl-$C_1$-$C_2$-alkyl- group, the heteroaryl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, and $C_1$-$C_3$-alkoxy-;

d) a $C_3$-$C_6$-cycloalkyl-$C_1$-$C_2$-alkyl- group, the $C_3$-$C_6$-cycloalkyl group of which is optionally substituted with one or two or three substituents, identically or differently, selected from the group consisting of halogen, $C_1$-$C_3$-alkyl-, $C_1$-$C_3$-alkoxy-, fluoro-$C_1$-$C_2$-alkyl-, and $C_1$-$C_2$-fluoroalkoxy-; and e) a heterocyclyl-$C_1$-$C_2$-alkyl- group, the heterocyclyl group of which is optionally substituted with one or two or three substituents, identically or differently, selected from the group consisting of halogen, $C_1$-$C_3$-alkyl-, $C_1$-$C_3$-alkoxy-, fluoro-$C_1$-$C_2$-alkyl-, and $C_1$-$C_2$-fluoroalkoxy-;

$R^{9a}$ and $R^{9b}$ are, independently from each other, a group selected from a hydrogen atom, fluoro atom, chloro atom, bromo atom, cyano, $C_1$-$C_3$-alkyl-, $C_1$-$C_3$-alkoxy-, fluoro-$C_1$-$C_2$-alkyl-, and $C_1$-$C_2$-fluoroalkoxy-; and $R_{10}$ is a group selected from $C_1$-$C_4$-alkyl-, fluoro-$C_1$-$C_3$-alkyl-, $C_3$-$C_7$-cycloalkyl-, heterocyclyl-, phenyl, benzyl and heteroaryl,
wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, and $C_1$-$C_2$-fluoroalkoxy-.

3. The compound of formula (I) according to claim 1, or an enantiomer, diastereomer, salt, solvate or salt of solvate thereof, wherein:
$R^{9a}$ and $R^{9b}$ are each a hydrogen atom.

4. The compound of formula (I) according to claim 1, or an enantiomer, diastereomer, salt, solvate or salt of solvate thereof, wherein:

$R^1$ is a $C_1$-$C_6$-alkyl or $C_3$-$C_5$-cycloalkyl group,
wherein said group is optionally substituted with one substituent selected from the group consisting of hydroxy, $C_1$-$C_3$-alkoxy-, —$NH_2$, alkylamino-, dialkylamino-, cyclic amines, and —OP(=O)(OH)$_2$;

$R^2$ is a group selected from

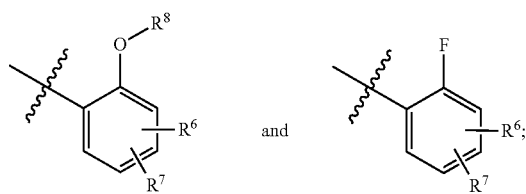

$R^3$ is a group selected from a fluoro atom, chloro atom, —$SF_5$, $C_1$-$C_3$-alkyl and fluoro-$C_1$-$C_3$-alkyl-;

$R^4$ is a hydrogen atom or fluoro atom;

$R^5$ is a group selected from a hydrogen atom, cyano, $C_1$-$C_4$-alkyl-, $C_3$-$C_4$-alkynyl-, $C_3$-$C_5$-cycloalkyl-, and phenyl,
wherein said $C_1$-$C_4$-alkyl, $C_3$-$C_5$-cycloalkyl- or phenyl group is optionally substituted with one, two or three substituents, identically or differently, selected from the group consisting of halogen, hydroxy, cyano, $C_1$-$C_3$-alkyl-, and $C_1$-$C_3$-alkoxy-;

$R^6$ and $R^7$ are, independently from each other, a group selected from a hydrogen atom, fluoro atom and chloro atom; and $R^8$ is a group selected from
  a) a $C_1$-$C_4$-alkyl group, which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, $C_1$-$C_3$-alkoxy-, $C_2$-$C_3$-alkenyl-, $C_2$-$C_3$-alkynyl-, and $C_3$-$C_5$-cycloalkyl-; and
  b) a phenyl-$C_1$-$C_2$-alkyl- group, the phenyl group of which is optionally substituted with one or two or three substituents, identically or differently, selected from the group consisting of halogen, hydroxy, —$NH_2$, alkylamino-, dialkylamino-, cyclic amines, cyano, $C_1$-$C_3$-alkyl-, fluoro-$C_1$-$C_2$-alkyl-, $C_1$-$C_2$-fluoroalkoxy-, and $C_1$-$C_3$-alkoxy-.

5. The compound of formula (I) according to claim 1, or an enantiomer, diastereomer, salt, solvate or salt of solvate thereof, wherein:

$R^1$ is a $C_1$-$C_6$-alkyl group,
wherein said group is optionally substituted with one substituent selected from the group consisting of $C_1$-$C_3$-alkoxy-, —$NH_2$, alkylamino-, dialkylamino- and cyclic amines;

$R^2$ is a group selected from

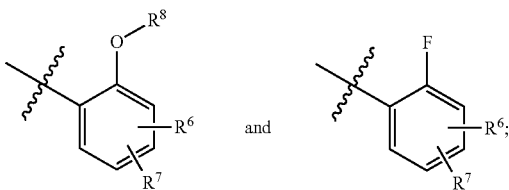

$R^3$ is a group selected from a fluoro atom, chloro atom, —$SF_5$, methyl and trifluoromethyl- group;

$R^4$ is a hydrogen atom or fluoro atom;

$R^5$ is a group selected from a hydrogen atom, cyano, $C_1$-$C_4$-alkyl-, $C_3$-$C_4$-alkynyl-, and phenyl,
wherein said $C_1$-$C_4$-alkyl or phenyl group is optionally substituted with one substituent selected from the group consisting of a fluoro atom, chloro atom, bromo atom, hydroxy, cyano, methyl, and methoxy-;

$R^6$ and $R^7$ are, independently from each other, a group selected from a hydrogen atom, fluoro atom and chloro atom;

$R^8$ is a group selected from
  a) a $C_1$-$C_4$-alkyl group, which is optionally substituted with one substituent selected from the group consisting of hydroxy, —$NH_2$, alkylamino-, dialkylamino-, cyano, $C_1$-$C_2$-alkoxy-, and $C_3$-$C_5$-cycloalkyl-; and
  b) a phenyl-$C_1$-$C_2$-alkyl- group, the phenyl group of which is optionally substituted with one substituent selected from the group consisting of halogen, hydroxy, —$NH_2$, alkylamino-, dialkylamino-, cyano, methyl-, trifluoromethyl-, trifluoromethoxy-, and methoxy-.

6. The compound of formula (I) according to claim 1, or an enantiomer, diastereomer, salt, solvate or salt of solvate thereof, wherein:

$R^1$ is a $C_1$-$C_3$-alkyl group;

$R^2$ is a group selected from

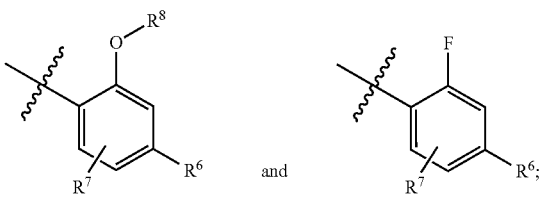

$R^3$ is a group selected from a fluoro atom, chloro atom, —$SF_5$ and trifluoromethyl- group;

$R^4$ is a hydrogen atom;

$R^5$ is a group selected from a hydrogen atom, cyano, $C_1$-$C_4$-alkyl-, $C_3$-$C_4$-alkynyl-, and phenyl,
wherein said $C_1$-$C_4$-alkyl or phenyl group is optionally substituted with one substituent selected from the group consisting of a fluoro atom, hydroxy, cyano, methyl, and methoxy-;

$R^6$ is a group selected from a hydrogen atom, fluoro atom and chloro atom;

$R^7$ is a hydrogen atom; and $R^8$ is a $C_1$-$C_3$-alkyl group.

7. The compound of formula (I) according claim 1, or an enantiomer, diastereomer, salt, solvate or salt of solvate thereof, wherein:

$R^6$ is a fluoro atom; and $R^7$ is a hydrogen atom.

8. The compound of formula (I) according to claim 1, or an enantiomer, diastereomer, salt, solvate or salt of solvate thereof, wherein:

$R^3$ is a group selected from a fluoro atom and —$SF_5$.

9. The compound of formula (I) according to claim 1, or an enantiomer, diastereomer, salt, solvate or salt of solvate thereof, wherein:

$R^1$ is a $C_1$-$C_3$-alkyl group;

$R^2$ is a group selected from

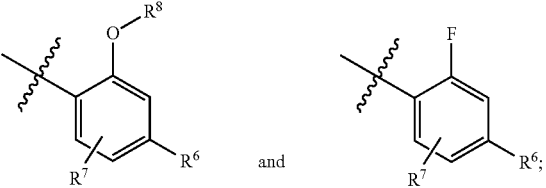

$R^3$ is a group selected from a fluoro atom and —$SF_5$;

$R^4$ is a hydrogen atom;

$R^5$ is a group selected from a hydrogen atom, cyano, $C_1$-$C_3$-alkyl-, prop-2-yn-1-yl-, and phenyl,
wherein said $C_1$-$C_3$-alkyl group is optionally substituted with one hydroxy group;

$R^6$ is a fluoro atom;

$R^7$ is a hydrogen atom; and $R^8$ is a $C_1$-$C_3$-alkyl group.

10. The compound of formula (I) according to claim 1, or an enantiomer, diastereomer, salt, solvate or salt of solvate thereof, wherein:
R¹ is a methyl group;
R² is a group selected from

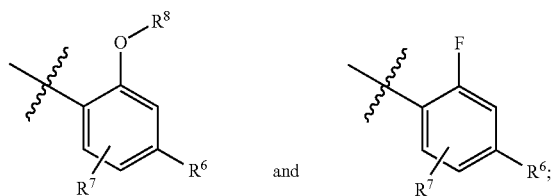

R³ is a group selected from a fluoro atom and —SF₅;
R⁴ is a hydrogen atom;
R⁵ is a group selected from a hydrogen atom, cyano, methyl, 3-hydroxypropyl-, prop-2-yn-1-yl-, and phenyl;
R⁶ is a fluoro atom;
R⁷ is a hydrogen atom; and
R⁸ is a methyl group.

11. The compound of formula (I) according to claim 1, which is selected from the group consisting of
5-Fluoro-4-(4-fluoro-2-methoxyphenyl)-N-{3-fluoro-5 [(S-methylsulfonodiimidoyl)methyl] phenyl}pyrimidin-2-amine;
(rac)-N-{3-[(N,S-Dimethylsulfonodiimidoyl)methyl]-5-fluorophenyl}-5-fluoro-4-(4-fluoro-2-methoxyphenyl) pyrimidin-2-amine;
(rac)-5-Fluoro-4-(4-fluoro-2-methoxyphenyl)-N-{3-fluoro-5-[S-methyl-N-phenylsulfonodiimidoyl) methyl]phenyl}pyrimidin-2-amine;
(rac)-5-Fluoro-4-(4-fluoro-2-methoxyphenyl)-N-(3-fluoro-5-{[S-methyl-N-(prop-2-yn-1-yl)sulfonodiimidoyl]methyl}phenyl)pyrimidin-2-amine;
(rac)-[(3-Fluoro-5-{[5-fluoro-4-(4-fluoro-2-methoxyphenyl)pyrimidin-2-yl]amino}benzyl)(imino)methyl-λ⁶-sulfanylidene]cyanamide;
(rac)-3-{[(3-Fluoro-5-{[5-fluoro-4-(4-fluoro-2-methoxyphenyl)pyrimidin-2-yl]amino}benzyl)(imino)methyl-λ⁶-sulfanylidene]amino}propan-1-ol;
4-(2,4-Difluorophenyl)-5-fluoro-N-{3[(S-methylsulfonodiimidoyl)methyl]-5-(pentafluoro-λ⁶-sulfanyl) phenyl}pyrimidin-2-amine; and
5-Fluoro-4-(4-fluoro-2-methoxyphenyl)-N-{3-[(S-methylsulfonodiimidoyl)methyl]-5-(pentafluoro-λ⁶-sulfanyl)phenyl}pyrimidin-2-amine;
or an enantiomer, diastereomer, salt, solvate or salt of solvate thereof.

12. A method for treatment of a hyper-proliferative disorder selected from the group consisting of lung carcinoma, prostate carcinoma, cervical carcinoma, colorectal carcinoma, melanoma, and ovarian carcinoma, comprising administering to a subject an effective amount of the compound of formula (I) according to claim 1, or an enantiomer, diastereomer, salt, solvate or salt of solvate thereof.

13. The method according to claim 12, wherein the method is for treatment of non-small cell lung carcinoma, hormone-independent human prostate carcinoma, multidrug-resistant human cervical carcinoma, and human acute myeloid leukemia.

14. A pharmaceutical combination comprising the compound of formula (I) according to claim 1, or an enantiomer, diastereomer, salt, solvate or salt of solvate thereof, in combination with at least one or more further active ingredients.

15. The method of claim 12, wherein the method comprises administering to the subject an effective amount of the compound of formula (I), or an enantiomer, diastereomer, salt, solvate or salt of solvate thereof, in combination with at least one or more further active ingredients.

16. A pharmaceutical composition comprising the compound of formula (I) according to claim 1, or an enantiomer, diastereomer, salt, solvate or salt of solvate thereof, in combination with an inert, nontoxic, pharmaceutically suitable adjuvant.

17. The method of claim 12, wherein the method comprises administering to the subject an effective amount of the compound of formula (I), or an enantiomer, diastereomer, salt, solvate or salt of solvate thereof, in combination with an inert, nontoxic, pharmaceutically suitable adjuvant.

18. A compound of formula 6

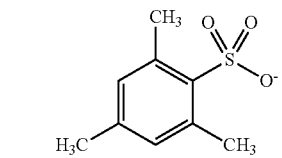

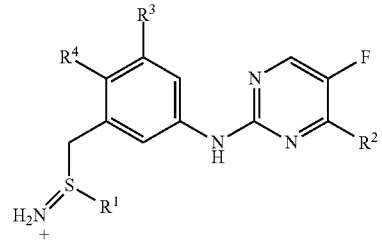

6 wherein:
R¹ is a group selected from $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —NH₂, alkylamino-, dialkylamino-, acetylamino-, N-methyl-N-acetylamino-, cyclic amines, —OP(=O)(OH)₂, —C(=O)OH, and —C(=O)NH₂;

R² is a group selected from

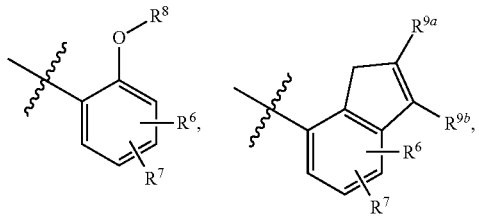

-continued

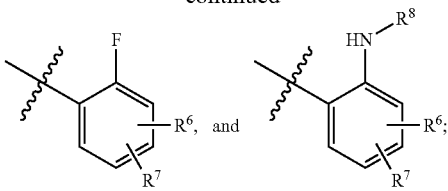

R³ is a group selected from a fluoro atom, chloro atom, bromo atom, cyano, —SF₅C₁-C₃-alkyl-, C₁-C₃-alkoxy-, halo-C₁-C₃-alkyl-, and C₁-C₃-fluoroalkoxy-;
R⁴ is a group selected from a hydrogen atom, fluoro atom, chloro atom, bromo atom, cyano, C₁-C₃-alkyl-, C₁-C₃-alkoxy-, halo-C₁-C₃-alkyl-, and C₁-C₃-fluoroalkoxy-,
R⁶ and R⁷ are, independently from each other, a group selected from a hydrogen atom, fluoro atom, chloro atom, bromo atom, cyano, C₁-C₃-alkyl-, C₁-C₃-alkoxy-, halo-C₁-C₃-alkyl-, and C₁-C₃-fluoroalkoxy-;
R⁸ is a group selected from
 a) a C₁-C₆-alkyl group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, C₁-C₃-alkyl-, halo-C₁-C₃-alkyl-, C₁-C₃-fluoroalkoxy-, C₁-C₃-alkoxy-, C₂-C₃-alkenyl-, C₂-C₃-alkynyl-, C₃-C₇-cycloalkyl-, heterocyclyl-, phenyl, and heteroaryl,
  wherein said C₃-C₇-cycloalkyl-, heterocyclyl-, phenyl or heteroaryl group is optionally substituted with one, two or three substituents, identically or differently, selected from the group consisting of halogen, hydroxy, C₁-C₃-alkyl-, C₁-C₃-alkoxy-, —NH₂, alkylamino-, dialkylamino-, acetylamino-, N-methyl-N-acetylamino-, cyclic amines, halo-C₁-C₃-alkyl-, and C₁-C₃-fluoroalkoxy-;
 b) a phenyl-C₁-C₃-alkyl- group, the phenyl group of which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, C₁-C₃-alkyl-, halo-C₁-C₃-alkyl-, C₁-C₃-fluoroalkoxy-, and C₁-C₃-alkoxy-;
 c) a heteroaryl-C₁-C₃-alkyl- group, the heteroaryl group of which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, C₁-C₃-alkyl-, halo-C₁-C₃-alkyl-, C₁-C₃-fluoroalkoxy-, and C₁-C₃-alkoxy-;
 d) a C₃-C₆-cycloalkyl-C₁-C₃-alkyl- group, the C₃-C₆-cycloalkyl group of which is optionally substituted with one or two or three substituents, identically or differently, selected from the group consisting of halogen, C₁-C₃-alkyl-, C₁-C₃-alkoxy-, halo-C₁-C₃-alkyl-, and C₁-C₃-fluoroalkoxy-; and
 e) a heterocyclyl-C₁-C₃-alkyl- group, the heterocyclyl group of which is optionally substituted with one or two or three substituents, identically or differently, selected from the group consisting of halogen, C₁-C₃-alkyl-, C₁-C₃-alkoxy-, halo-C₁-C₃-alkyl-, and C₁-C₃-fluoroalkoxy-; and $R^{9a}$ and $R^{9b}$ are, independently from each other, a group selected from a hydrogen atom, fluoro atom, chloro atom, bromo atom, cyano, C₁-C₃-alkyl-, C₁-C₃-alkoxy-, halo-C₁-C₃-alkyl-, and C₁-C₃-fluoroalkoxy-,
or an enantiomer, diastereomer or solvate thereof.

19. A process for preparing the compound of formula 6, comprising reacting a compound of formula 5,

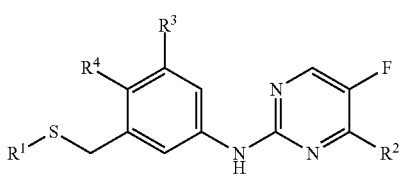

5 wherein R¹, R², R³ and R⁴ are as defined for the compound of formula 6 according to claim 18, with O-mesitylenesulfonyl hydroxylamine, in a chlorinated aliphatic hydrocarbon of formula chloro-C₁-C₂-alkyl-H, to form the compound of formula 6

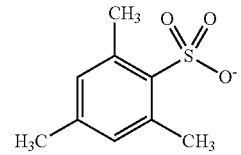

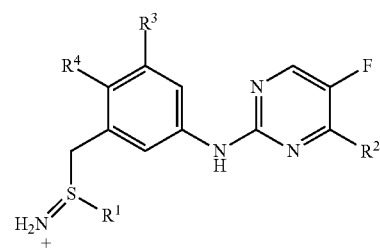

6 wherein R¹, R², R³ and R⁴ are as defined for the compound of formula 6 according to claim 18.

20. A process for preparing a compound of formula (Ia), or an enantiomer, diastereomer, salt, solvate or salt of solvate thereof, comprising oxidizing a compound of formula 6

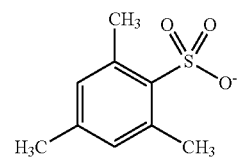

-continued

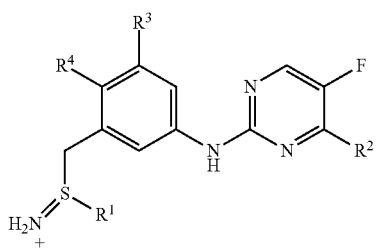

wherein $R^1$, $R^2$, $R^3$ and $R^4$ are as defined for the compound of formula (I) according to claim 1, by treatment with N-chloro succinimide, in N,N-dimethylformamide (DMF), N,N-dimethylacetamide or N-methylpyrrolidin-2-one, or a mixture thereof, as a solvent, in the presence of an alkali carbonate, followed by addition of hexamethyldisilazene, to form the compound of formula (Ia)

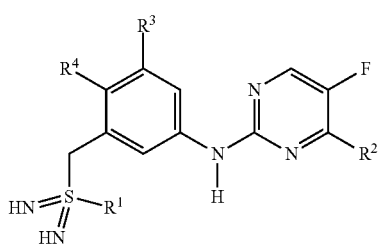

(Ia)

wherein $R^1$, $R^2$, $R^3$ and $R^4$ are as defined for the compound of formula (I) according to claim 1, wherein the resulting compound of formula (Ia) is optionally, if appropriate, treated with the corresponding (i) solvents and/or (ii) bases or acids to form a solvate, salt and/or solvate of the salt thereof.

21. A process for preparing the compound of formula (I), or an enantiomer, diastereomer, salt, solvate or salt of solvate thereof, comprising oxidizing a compound of formula 6

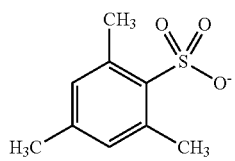

-continued

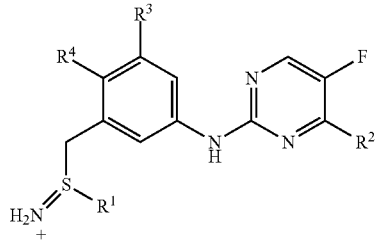

wherein $R^1$, $R^2$, $R^3$ and $R^4$ are as defined for the compound of formula (I) according to claim 1, by treatment with N-chloro succinimide, in N,N-dimethylformamide (DMF), N,N-dimethylacetamide or N-methylpyrrolidin-2-one, or a mixture thereof, as a solvent, in the presence of an alkali carbonate, followed by addition of an amine of formula $R^5$—$NH_2$, wherein $R^5$ is as defined for the compound of formula (I) according to claim 1, to give the compound of formula (I)

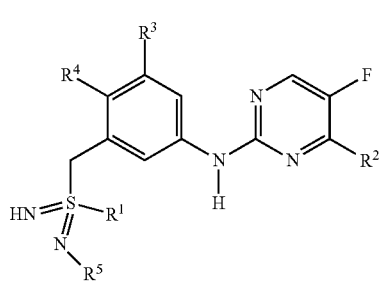

(I)

wherein $R^1$, $R^2$, $R^3$ and $R^4$ are as defined for the compound of formula (I) according to claim 1, wherein the resulting compound of formula (I) is optionally, if appropriate, treated with the corresponding (i) solvents and/or (ii) bases or acids to form a solvate, salt and/or solvate of the salt thereof.

22. The compound of formula (I) according to claim 1 or a salt thereof.

23. The compound of formula (I) according to claim 11 or a salt thereof.

24. The method according to claim 12, comprising administering to the subject an effective amount of the compound of formula (I) or salt thereof.

25. The pharmaceutical combination according to claim 14, comprising the compound of formula (I), or a salt thereof, in combination with at least one or more further active ingredients.

26. The pharmaceutical composition according to claim 16, comprising the compound of formula (I), or a salt thereof, in combination with an inert, nontoxic, pharmaceutically suitable adjuvant.

* * * * *